(12) United States Patent
Sowards et al.

(10) Patent No.: US 12,285,572 B2
(45) Date of Patent: Apr. 29, 2025

(54) OPTICAL-FIBER STYLET HOLDERS AND METHODS THEREOF

(71) Applicant: Bard Access Systems, Inc., Salt Lake City, UT (US)

(72) Inventors: Steffan Sowards, Salt Lake City, UT (US); Anthony K. Misener, Bountiful, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 487 days.

(21) Appl. No.: 17/529,022

(22) Filed: Nov. 17, 2021

(65) Prior Publication Data

US 2022/0152349 A1    May 19, 2022

Related U.S. Application Data

(60) Provisional application No. 63/115,442, filed on Nov. 18, 2020.

(51) Int. Cl.
*A61M 25/01* (2006.01)
*A61B 1/07* (2006.01)

(52) U.S. Cl.
CPC ........... *A61M 25/0102* (2013.01); *A61B 1/07* (2013.01)

(58) Field of Classification Search
CPC .... A61B 2034/2061; A61B 2562/0266; A61B 5/6852; A61B 1/07; A61B 5/0084; A61B 2034/2055; A61B 46/23; A61B 2090/306; A61B 2046/234; A61B 5/1079; A61B 5/1455; A61B 1/00167; A61M 2025/0166; A61M 25/01; A61M 2025/0063; A61M 2025/0293; A61M 2025/09125; A61N 2005/063; G02B 6/4202; G02B 6/4203; G02B 6/4219; G02B 6/4226
See application file for complete search history.

(56) References Cited

U.S. PATENT DOCUMENTS 3,493,288 A    2/1970 Oltman et al.
4,768,855 A *  9/1988 Nishi ................... G02B 6/2555
                                                  385/137

(Continued)

FOREIGN PATENT DOCUMENTS

CA         3025240 A1    11/2017
DE     102016109601 A1   11/2017

(Continued)

OTHER PUBLICATIONS

PCT/US2021 /059755 filed Nov. 17, 2021 International Search Report and Written Opinion dated Apr. 29, 2022.

(Continued)

*Primary Examiner* — Gerald Johnson
(74) *Attorney, Agent, or Firm* — Rutan & Tucker LLP

(57) ABSTRACT

Disclosed herein are optical-fiber stylet holders and methods thereof for holding optical-fiber stylets in position in catheters or the like while preventing breakage of optical fibers in the optical-fiber stylets and maintaining functionality of the optical-fiber stylets. The holding of optical-fiber stylets in position in catheters or the like can be important for maintaining distal tips of intravascularly delivered optical-fiber stylets in their target anatomical locations during procedures.

19 Claims, 8 Drawing Sheets

(56) References Cited

U.S. PATENT DOCUMENTS

| | | |
|---|---|---|
| 4,813,429 A | 3/1989 | Eshel et al. |
| 5,099,845 A | 3/1992 | Besz et al. |
| 5,163,935 A | 11/1992 | Black et al. |
| 5,178,153 A | 1/1993 | Einzig |
| 5,207,672 A | 5/1993 | Roth et al. |
| 5,211,165 A | 5/1993 | Dumoulin et al. |
| 5,220,703 A | 6/1993 | Kanayama et al. |
| 5,275,151 A | 1/1994 | Shockey et al. |
| 5,295,212 A | 3/1994 | Morton et al. |
| 5,423,321 A | 6/1995 | Fontenot |
| 5,454,807 A | 10/1995 | Lennox et al. |
| 5,517,997 A | 5/1996 | Fontenot |
| 5,599,492 A | 2/1997 | Engelson |
| 5,622,170 A | 4/1997 | Schulz |
| 5,633,494 A | 5/1997 | Danisch |
| 5,693,043 A | 12/1997 | Kittrell et al. |
| 5,740,808 A | 4/1998 | Panescu et al. |
| 5,827,313 A | 10/1998 | Ream |
| 5,872,879 A | 2/1999 | Hamm |
| 5,873,842 A | 2/1999 | Brennen et al. |
| 5,879,306 A | 3/1999 | Fontenot et al. |
| 5,906,579 A | 5/1999 | Vander Salm et al. |
| 5,957,831 A | 9/1999 | Adair |
| 6,069,698 A | 5/2000 | Ozawa et al. |
| 6,081,741 A | 6/2000 | Hollis |
| 6,178,346 B1 | 1/2001 | Amundson et al. |
| 6,208,887 B1 | 3/2001 | Clarke |
| 6,210,362 B1 | 4/2001 | Ponzi |
| 6,319,227 B1 | 11/2001 | Mansouri-Ruiz |
| 6,343,227 B1 | 1/2002 | Crowley |
| 6,398,721 B1 | 6/2002 | Nakamura et al. |
| 6,485,482 B1 | 11/2002 | Belef |
| 6,564,089 B2 | 5/2003 | Zatt et al. |
| 6,593,884 B1 | 7/2003 | Gilboa et al. |
| 6,597,941 B2 | 7/2003 | Fontenot et al. |
| 6,619,857 B2 | 9/2003 | Miyake |
| 6,650,923 B1 | 11/2003 | Lesh et al. |
| 6,685,666 B1 | 2/2004 | Fontenot |
| 6,687,010 B1 | 2/2004 | Horii et al. |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 6,975,803 B2 | 12/2005 | Koide et al. |
| 7,132,645 B2 | 11/2006 | Korn |
| 7,273,056 B2 | 9/2007 | Wilson et al. |
| 7,344,533 B2 | 3/2008 | Pearson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 | 5/2009 | Ainsworth et al. |
| 7,587,236 B2 | 9/2009 | Demos et al. |
| 7,603,166 B2 | 10/2009 | Casscells, III et al. |
| 7,699,855 B2 | 4/2010 | Anderson et al. |
| 7,729,735 B1 | 6/2010 | Burchman |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,054,469 B2 | 11/2011 | Nakabayashi et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,187,189 B2 | 5/2012 | Jung et al. |
| 8,197,494 B2 | 6/2012 | Jaggi et al. |
| 8,267,932 B2 | 9/2012 | Baxter et al. |
| 8,369,932 B2 | 2/2013 | Cinbis et al. |
| 8,388,541 B2 | 3/2013 | Messerly et al. |
| 8,571,640 B2 | 10/2013 | Holman |
| 8,597,315 B2 | 12/2013 | Snow et al. |
| 8,700,358 B1 | 4/2014 | Parker, Jr. |
| 8,781,555 B2 | 7/2014 | Burnside et al. |
| 8,798,721 B2 | 8/2014 | Dib |
| 8,968,331 B1 | 3/2015 | Sochor |
| 8,979,871 B2 | 3/2015 | Tyc et al. |
| 9,119,551 B2 | 9/2015 | Qi et al. |
| 9,186,046 B2 | 11/2015 | Ramamurthy et al. |
| 9,339,206 B2 | 5/2016 | Grunwald |
| 9,345,510 B2 | 5/2016 | Patel et al. |
| 9,360,630 B2 | 6/2016 | Jenner et al. |
| 9,549,685 B2 | 1/2017 | Cox et al. |
| 9,560,954 B2 | 2/2017 | Jacobs et al. |
| 9,572,492 B2 | 2/2017 | Simpson et al. |
| 9,622,706 B2 | 4/2017 | Dick et al. |
| 9,645,326 B1 | 5/2017 | Sausse et al. |
| 9,649,048 B2 | 5/2017 | Cox et al. |
| 9,678,275 B1 | 6/2017 | Griffin |
| 9,678,284 B2 | 6/2017 | Coggi et al. |
| 9,872,978 B1* | 1/2018 | Zaborsky ................. G02B 6/02 |
| 10,231,643 B2 | 3/2019 | Grunwald |
| 10,231,753 B2 | 3/2019 | Burnside et al. |
| 10,258,240 B1 | 4/2019 | Eberle et al. |
| 10,265,133 B1 | 4/2019 | McClellan |
| 10,327,830 B2 | 6/2019 | Grant et al. |
| 10,349,890 B2 | 7/2019 | Misener et al. |
| 10,448,837 B2 | 10/2019 | Manzke et al. |
| 10,492,876 B2 | 12/2019 | Anastassiou et al. |
| 10,568,586 B2 | 2/2020 | Begin et al. |
| 10,603,126 B2 | 3/2020 | Karguth et al. |
| 10,620,386 B2 | 4/2020 | Van Der Mark et al. |
| 10,631,718 B2 | 4/2020 | Petroff et al. |
| 10,932,670 B2 | 3/2021 | Smith et al. |
| 10,939,889 B2 | 3/2021 | Flexman et al. |
| 10,992,078 B2 | 4/2021 | Thompson et al. |
| 10,992,079 B2 | 4/2021 | Stats et al. |
| 11,000,207 B2 | 5/2021 | Burnside et al. |
| 11,000,265 B1 | 5/2021 | Ryu et al. |
| 11,103,321 B2 | 8/2021 | Braun et al. |
| 11,123,047 B2 | 9/2021 | Jaffer et al. |
| 11,259,892 B2 | 3/2022 | Hufford et al. |
| 11,284,916 B2 | 3/2022 | Patel et al. |
| 11,382,653 B2 | 7/2022 | Patel et al. |
| 11,474,310 B2 | 10/2022 | Sowards et al. |
| 11,525,670 B2 | 12/2022 | Messerly et al. |
| 11,547,282 B2 | 1/2023 | Weise et al. |
| 11,607,150 B2 | 3/2023 | Schweikert et al. |
| 11,621,518 B2 | 4/2023 | Stats et al. |
| 11,707,205 B2 | 7/2023 | Messerly et al. |
| 11,806,096 B2 | 11/2023 | Flatt et al. |
| 11,850,073 B2 | 12/2023 | Wright et al. |
| 11,931,112 B2 | 3/2024 | Thompson et al. |
| 2002/0019627 A1 | 2/2002 | Maguire et al. |
| 2002/0087206 A1* | 7/2002 | Hirschberg .......... A61N 5/1015 |
| | | 607/89 |
| 2002/0166190 A1 | 11/2002 | Miyake et al. |
| 2002/0188285 A1 | 12/2002 | Brown |
| 2002/0198457 A1 | 12/2002 | Tearney et al. |
| 2003/0045798 A1 | 3/2003 | Hular et al. |
| 2003/0092995 A1 | 5/2003 | Thompson |
| 2004/0111020 A1 | 6/2004 | Long |
| 2004/0111147 A1 | 6/2004 | Rabkin et al. |
| 2004/0242995 A1 | 12/2004 | Maschke |
| 2004/0260182 A1 | 12/2004 | Zuluaga et al. |
| 2005/0033264 A1 | 2/2005 | Redinger |
| 2006/0013523 A1 | 1/2006 | Childers et al. |
| 2006/0036164 A1 | 2/2006 | Wilson et al. |
| 2006/0100610 A1 | 5/2006 | Wallace et al. |
| 2006/0189959 A1 | 8/2006 | Schneiter |
| 2006/0200049 A1 | 9/2006 | Leo et al. |
| 2006/0241395 A1 | 10/2006 | Kruger et al. |
| 2006/0241492 A1 | 10/2006 | Boese et al. |
| 2007/0060847 A1 | 3/2007 | Leo et al. |
| 2007/0156019 A1 | 7/2007 | Larkin et al. |
| 2007/0179485 A1 | 8/2007 | Yeik et al. |
| 2007/0201793 A1 | 8/2007 | Askins et al. |
| 2007/0253673 A1* | 11/2007 | Nielsen ................. G02B 6/4248 |
| | | 385/134 |
| 2007/0287886 A1 | 12/2007 | Saadat |
| 2007/0299425 A1 | 12/2007 | Waner et al. |

(56) References Cited

U.S. PATENT DOCUMENTS

| | | |
|---|---|---|
| 2008/0034519 A1 | 2/2008 | Fujiwara |
| 2008/0172119 A1 | 7/2008 | Yamasaki et al. |
| 2008/0183128 A1 | 7/2008 | Morriss et al. |
| 2008/0281293 A1 | 11/2008 | Peh et al. |
| 2008/0285909 A1 | 11/2008 | Younge et al. |
| 2009/0005675 A1 | 1/2009 | Grunwald et al. |
| 2009/0018393 A1 | 1/2009 | Dick et al. |
| 2009/0046980 A1* | 2/2009 | Rohlen ............... A61B 5/6852 385/52 |
| 2009/0062634 A1 | 3/2009 | Say et al. |
| 2009/0137952 A1 | 5/2009 | Ramamurthy et al. |
| 2009/0208143 A1 | 8/2009 | Yoon et al. |
| 2009/0227992 A1 | 9/2009 | Nir et al. |
| 2009/0234328 A1 | 9/2009 | Cox et al. |
| 2009/0253967 A1 | 10/2009 | Gill et al. |
| 2009/0304582 A1 | 12/2009 | Rousso et al. |
| 2009/0318757 A1 | 12/2009 | Singh |
| 2009/0324161 A1 | 12/2009 | Prisco |
| 2010/0016729 A1 | 1/2010 | Futrell |
| 2010/0030063 A1 | 2/2010 | Lee et al. |
| 2010/0063534 A1 | 3/2010 | Kugler et al. |
| 2010/0114115 A1 | 5/2010 | Schlesinger et al. |
| 2010/0114190 A1 | 5/2010 | Bendett et al. |
| 2010/0139669 A1 | 6/2010 | Piferi et al. |
| 2010/0204569 A1 | 8/2010 | Burnside et al. |
| 2010/0286531 A1 | 11/2010 | Ryan et al. |
| 2010/0292758 A1 | 11/2010 | Lee et al. |
| 2011/0087112 A1 | 4/2011 | Leo et al. |
| 2011/0098533 A1 | 4/2011 | Onoda et al. |
| 2011/0144481 A1 | 6/2011 | Feer et al. |
| 2011/0144630 A1* | 6/2011 | Loeb .................... A61B 18/22 606/16 |
| 2011/0166442 A1 | 7/2011 | Sarvazyan |
| 2011/0172680 A1 | 7/2011 | Younge et al. |
| 2011/0178509 A1 | 7/2011 | Zerfas et al. |
| 2011/0196248 A1 | 8/2011 | Grunwald |
| 2011/0245662 A1 | 10/2011 | Eggers et al. |
| 2011/0295108 A1 | 12/2011 | Cox et al. |
| 2012/0046562 A1 | 2/2012 | Powers et al. |
| 2012/0143029 A1 | 6/2012 | Silverstein et al. |
| 2012/0184827 A1 | 7/2012 | Shwartz et al. |
| 2012/0184955 A1 | 7/2012 | Pivotto et al. |
| 2012/0321243 A1 | 12/2012 | Younge et al. |
| 2013/0096482 A1 | 4/2013 | Bertrand et al. |
| 2013/0104884 A1 | 5/2013 | Vazales et al. |
| 2013/0150732 A1 | 6/2013 | Manzke et al. |
| 2013/0188855 A1 | 7/2013 | Desjardins et al. |
| 2013/0190741 A1 | 7/2013 | Moll et al. |
| 2013/0204124 A1 | 8/2013 | Duindam et al. |
| 2013/0211246 A1 | 8/2013 | Parasher |
| 2013/0296652 A1 | 11/2013 | Farr |
| 2013/0296693 A1 | 11/2013 | Wenzel et al. |
| 2013/0310668 A1 | 11/2013 | Young |
| 2013/0324840 A1 | 12/2013 | Zhongping et al. |
| 2014/0031674 A1 | 1/2014 | Newman et al. |
| 2014/0046261 A1 | 2/2014 | Newman et al. |
| 2014/0058368 A1 | 2/2014 | Hogue |
| 2014/0088413 A1 | 3/2014 | Von Bucsh et al. |
| 2014/0121468 A1 | 5/2014 | Eichenholz |
| 2014/0155948 A1 | 6/2014 | Walsh et al. |
| 2014/0188133 A1 | 7/2014 | Misener |
| 2014/0221829 A1 | 8/2014 | Maitland et al. |
| 2014/0259477 A1 | 9/2014 | Huang |
| 2014/0275997 A1 | 9/2014 | Chopra et al. |
| 2014/0318825 A1 | 10/2014 | Erb et al. |
| 2014/0378945 A1 | 12/2014 | Beri |
| 2015/0029511 A1 | 1/2015 | 'T Hooft et al. |
| 2015/0031987 A1 | 1/2015 | Pameijer et al. |
| 2015/0045649 A1 | 2/2015 | O'Dea et al. |
| 2015/0080688 A1 | 3/2015 | Cinbis et al. |
| 2015/0099979 A1 | 4/2015 | Caves et al. |
| 2015/0105654 A1 | 4/2015 | Meyer |
| 2015/0119700 A1 | 4/2015 | Liang et al. |
| 2015/0119724 A1 | 4/2015 | Weber et al. |
| 2015/0209113 A1 | 7/2015 | Burkholz et al. |
| 2015/0209117 A1 | 7/2015 | Flexman et al. |
| 2015/0244465 A1 | 8/2015 | Chou et al. |
| 2015/0270900 A1 | 9/2015 | Hilario et al. |
| 2015/0301288 A1 | 10/2015 | Thornton, Jr. |
| 2015/0305816 A1 | 10/2015 | Hadzic |
| 2015/0320977 A1 | 11/2015 | Vitullo et al. |
| 2016/0018602 A1 | 1/2016 | Govari et al. |
| 2016/0151115 A1 | 6/2016 | Karguth et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0256228 A1 | 9/2016 | Haartsen et al. |
| 2016/0262627 A1 | 9/2016 | Hecker et al. |
| 2016/0302762 A1 | 10/2016 | Stigall et al. |
| 2016/0331360 A1 | 11/2016 | Hera et al. |
| 2016/0354038 A1 | 12/2016 | Demirtas et al. |
| 2016/0357007 A1 | 12/2016 | Swanson |
| 2016/0374589 A1 | 12/2016 | Misener et al. |
| 2017/0017048 A1 | 1/2017 | Coggi et al. |
| 2017/0020394 A1 | 1/2017 | Harrington |
| 2017/0052091 A1 | 2/2017 | Mori |
| 2017/0079548 A1 | 3/2017 | Silverstein et al. |
| 2017/0082806 A1 | 3/2017 | Van Der Mark et al. |
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0303824 A1 | 10/2017 | Schlesinger et al. |
| 2017/0333136 A1 | 11/2017 | Hladio et al. |
| 2017/0348063 A1 | 12/2017 | Braun et al. |
| 2018/0067268 A1 | 3/2018 | Murakami et al. |
| 2018/0095231 A1 | 4/2018 | Lowell et al. |
| 2018/0113038 A1 | 4/2018 | Janabi-Sharifi et al. |
| 2018/0116551 A1 | 5/2018 | Newman et al. |
| 2018/0140170 A1 | 5/2018 | Van Putten et al. |
| 2018/0175547 A1 | 6/2018 | Hsu |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0289243 A1 | 10/2018 | Landey et al. |
| 2018/0289390 A1 | 10/2018 | Amorizzo et al. |
| 2018/0289927 A1 | 10/2018 | Messerly |
| 2018/0339134 A1 | 11/2018 | Leo |
| 2018/0360545 A1 | 12/2018 | Cole et al. |
| 2018/0369432 A1 | 12/2018 | Zaborsky |
| 2019/0008376 A1 | 1/2019 | Wortelboer et al. |
| 2019/0059743 A1 | 2/2019 | Ramachandran et al. |
| 2019/0110838 A1 | 4/2019 | Martinez et al. |
| 2019/0110839 A1 | 4/2019 | Rafii-Tari et al. |
| 2019/0110844 A1 | 4/2019 | Misener et al. |
| 2019/0142528 A1 | 5/2019 | Vertikov |
| 2019/0212761 A1 | 7/2019 | Swanson et al. |
| 2019/0223706 A1 | 7/2019 | Takeuchi et al. |
| 2019/0235182 A1 | 8/2019 | Cheng |
| 2019/0237902 A1 | 8/2019 | Thompson et al. |
| 2019/0271815 A1 | 9/2019 | Van Der Mark et al. |
| 2019/0321110 A1 | 10/2019 | Grunwald et al. |
| 2019/0343424 A1 | 11/2019 | Blumenkranz et al. |
| 2019/0357875 A1 | 11/2019 | Qi et al. |
| 2019/0374196 A1 | 12/2019 | Courtney et al. |
| 2020/0046434 A1 | 2/2020 | Graetzel et al. |
| 2020/0155073 A1 | 5/2020 | Hwang et al. |
| 2020/0170724 A1 | 6/2020 | Flatt et al. |
| 2020/0188036 A1 | 6/2020 | Ding et al. |
| 2020/0275827 A1 | 9/2020 | Weise et al. |
| 2020/0305983 A1 | 10/2020 | Yampolsky et al. |
| 2021/0007796 A1 | 1/2021 | Panescu et al. |
| 2021/0030504 A1 | 2/2021 | Thompson et al. |
| 2021/0045814 A1 | 2/2021 | Thompson et al. |
| 2021/0298680 A1 | 3/2021 | Sowards et al. |
| 2021/0154440 A1 | 5/2021 | Misener |
| 2021/0156676 A1 | 5/2021 | Messerly et al. |
| 2021/0205585 A1 | 7/2021 | Ullmann et al. |
| 2021/0215871 A1 | 7/2021 | Hayes et al. |
| 2021/0268229 A1 | 9/2021 | Sowards et al. |
| 2021/0271035 A1 | 9/2021 | Sowards et al. |

(56) References Cited

U.S. PATENT DOCUMENTS

| | | |
|---|---|---|
| 2021/0275256 A1 | 9/2021 | Sowards et al. |
| 2021/0275257 A1 | 9/2021 | Prior et al. |
| 2021/0278604 A1 | 9/2021 | Rohr Daniel et al. |
| 2021/0282867 A1 | 9/2021 | Tegg et al. |
| 2021/0290315 A1 | 9/2021 | Lampert et al. |
| 2021/0299879 A1 | 9/2021 | Pinter et al. |
| 2021/0325172 A1 | 10/2021 | Hendriks et al. |
| 2021/0330398 A1 | 10/2021 | Tegg et al. |
| 2021/0389519 A1 | 12/2021 | Choi et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0034733 A1 | 2/2022 | Misener et al. |
| 2022/0039632 A1 | 2/2022 | Polejaev et al. |
| 2022/0110695 A1 | 4/2022 | Sowards et al. |
| 2022/0110706 A1 | 4/2022 | Misener et al. |
| 2022/0133401 A1 | 5/2022 | O'Brien et al. |
| 2022/0160209 A1 | 5/2022 | Sowards et al. |
| 2022/0188285 A1 | 6/2022 | Ofenloch |
| 2022/0257975 A1 | 8/2022 | Croll et al. |
| 2022/0330891 A1 | 10/2022 | Sowards et al. |
| 2023/0082991 A1 | 3/2023 | Sowards et al. |
| 2023/0285085 A1 | 9/2023 | Misener et al. |
| 2023/0292997 A1 | 9/2023 | Sowards et al. |
| 2023/0293243 A1 | 9/2023 | Sowards et al. |
| 2023/0320663 A1 | 10/2023 | Misener et al. |
| 2023/0338090 A1 | 10/2023 | Misener et al. |
| 2023/0346314 A1 | 11/2023 | Sowards et al. |
| 2023/0346482 A1 | 11/2023 | Sowards et al. |
| 2023/0379057 A1 | 11/2023 | Moore |
| 2023/0414293 A1 | 12/2023 | Farley et al. |
| 2023/0417998 A1 | 12/2023 | Misener et al. |
| 2024/0016425 A1 | 1/2024 | Sowards et al. |
| 2024/0094475 A1 | 3/2024 | Misener et al. |
| 2024/0180470 A1 | 6/2024 | Sowards et al. |
| 2024/0215917 A1 | 7/2024 | Sowards et al. |
| 2024/0423456 A1 | 12/2024 | Sowards et al. |

FOREIGN PATENT DOCUMENTS

| | | |
|---|---|---|
| EP | 2240111 A2 | 10/2010 |
| EP | 2385802 B1 | 8/2013 |
| EP | 3266383 A1 | 1/2018 |
| EP | 3545849 A1 | 10/2019 |
| EP | 3725252 A1 | 10/2020 |
| WO | 99/64099 A1 | 12/1999 |
| WO | 1999064099 A1 | 12/1999 |
| WO | 2006080076 A1 | 8/2006 |
| WO | 2006122001 A2 | 11/2006 |
| WO | 2009/155325 A2 | 12/2009 |
| WO | 2011141830 A1 | 11/2011 |
| WO | 2011150376 A1 | 12/2011 |
| WO | 2012064769 A2 | 5/2012 |
| WO | 2012135339 A1 | 10/2012 |
| WO | 2013114376 A1 | 8/2013 |
| WO | 2014049555 A1 | 4/2014 |
| WO | 2015055413 A1 | 4/2015 |
| WO | 2015074045 A2 | 5/2015 |
| WO | 2016/061431 A1 | 4/2016 |
| WO | 2016193051 A1 | 12/2016 |
| WO | 2018071490 A1 | 4/2018 |
| WO | 2018/096491 A1 | 5/2018 |
| WO | 2019037071 A1 | 2/2019 |
| WO | 2019/046769 A1 | 3/2019 |
| WO | 2019230713 A1 | 12/2019 |
| WO | 2020/142470 A1 | 7/2020 |
| WO | 2021021408 A1 | 2/2021 |
| WO | 2021030092 A1 | 2/2021 |
| WO | 2021108688 A1 | 6/2021 |
| WO | 2021108697 A1 | 6/2021 |
| WO | 2021144317 A1 | 7/2021 |
| WO | 2021178578 A1 | 9/2021 |
| WO | 2022/031613 A1 | 2/2022 |
| WO | 2022/081586 A1 | 4/2022 |
| WO | 2022/081723 A1 | 4/2022 |
| WO | 2022109045 A1 | 5/2022 |
| WO | 2022115624 A1 | 6/2022 |
| WO | 2022221608 A1 | 10/2022 |
| WO | 2023043947 A1 | 3/2023 |
| WO | 2023172652 A1 | 9/2023 |
| WO | 2023177822 A1 | 9/2023 |
| WO | 2023177889 A1 | 9/2023 |
| WO | 2023200734 A1 | 10/2023 |
| WO | 2023205257 A1 | 10/2023 |
| WO | 2023212096 A1 | 11/2023 |
| WO | 2023212098 A1 | 11/2023 |
| WO | 2023249952 A1 | 12/2023 |
| WO | 2024015464 A1 | 1/2024 |
| WO | 2024123837 A1 | 6/2024 |

OTHER PUBLICATIONS

U.S. Appl. No. 17/185,777, filed Feb. 25, 2021 Notice of Allowance dated Jun. 10, 2022.
PCT/US2023/014849 filed Mar. 8, 2023 International Search Report and Written Opinion dated Jun. 7, 2023.
PCT/US2023/015416 filed Mar. 16, 2023 International Search Report and Written Opinion dated May 26, 2023.
PCT/US2023/015536 filed Mar. 17, 2023 International Search Report and Written Opinion dated Jun. 22, 2023.
PCT/US2023/018076 filed Apr. 10, 2023 International Search Report and Written Opinion dated Jul. 11, 2023.
PCT/US2023/019130 filed Apr. 19, 2023 International Search Report and Written Opinion dated Jul. 19, 2023.
PCT/US2023/020044 filed Apr. 26, 2023 International Search Report and Written Opinion dated Jul. 19, 2023.
U.S. Appl. No. 17/187,536, filed Feb. 26, 2021 Non-Final Office Action dated May 17, 2023.
U.S. Appl. No. 17/217,852, filed Mar. 30, 2021 Non Final Office Action dated Jun. 7, 2023.
U.S. Appl. No. 17/499,644, filed Oct. 12, 2021 Restriction Requirement dated Jul. 11, 2023.
U.S. Appl. No. 17/697,895, filed Mar. 17, 2022 Final Office Action dated Aug. 16, 2023.
U.S. Appl. No. 17/697,895, filed Mar. 17, 2022 Non Final Office Action dated Jun. 14, 2023.
PCT/US2021/024969 filed Mar. 30, 2021 International Search Report and Written Opinion dated Jul. 19, 2021.
PCT/US2021/054596 filed Oct. 12, 2021 International Search Report and Written Opinion dated Jan. 26, 2022.
PCT/US2022/043698 filed Sep. 15, 2022 International Search Report and Written Opinion dated Dec. 19, 2022.
U.S. Appl. No. 17/967,794, filed Oct. 17, 2022 Notice of Allowance dated Feb. 15, 2023.
PCT/US2022/024934 filed Apr. 14, 2022 International Search Report and Written Opinion dated Jul. 18, 2022.
PCT/US2023/020042 filed Apr. 26, 2023 International Search Report and Written Opinion dated Sep. 26, 2023.
PCT/US2023/025757 filed Jun. 20, 2023 International Search Report and Written Opinion dated Sep. 11, 2023.
PCT/US2023/027527 filed Jul. 12, 2023 International Search Report and Written Opinion dated Oct. 16, 2023.
U.S. Appl. No. 17/187,536, filed Feb. 26, 2021 Advisory Action dated Nov. 21, 2023.
U.S. Appl. No. 17/187,536, filed Feb. 26, 2021 Final Office Action dated Sep. 20, 2023.
U.S. Appl. No. 17/217,852, filed Mar. 30, 2021 Ex Parte Quayle Action dated Sep. 8, 2023.
U.S. Appl. No. 17/217,852, filed Mar. 30, 2021 Notice of Allowance dated Nov. 7, 2023.
U.S. Appl. No. 17/499,644, filed Oct. 12, 2021 Notice of Allowance dated Sep. 18, 2023.
U.S. Appl. No. 17/535,406, filed Nov. 24, 2021 Restriction Requirement dated Nov. 24, 2023.
U.S. Appl. No. 17/697,895, filed Mar. 17, 2022 Advisory Action dated Sep. 8, 2023.
PCT/US2021/038899 filed Jun. 24, 2021 International Search Report and Written Opinion dated Oct. 6, 2021.

(56) References Cited

OTHER PUBLICATIONS

PCT/US2021/044216 filed Aug. 2, 2021 International Search Report and Written Opinion dated Nov. 18, 2021.
PCT/US2021/054802 filed Oct. 13, 2021 International Search Report and Written Opinion dated Feb. 2, 2022.
PCT/US2021/060849 filed Nov. 24, 2021 International Search Report and Written Opinion dated Mar. 9, 2022.
U.S. Appl. No. 17/185,777, filed Feb. 25, 2021 Non-Final Office Action dated Feb. 9, 2022.
Kirill Bronnikov, Alexey Wolf, Sergey Yakushin, Alexandr Dostovalov, Olga Egorova, Sergey Zhuravlev, Sergey Semjonov, Stefan Wabnitz, and Sergey Babin, "Durable shape sensor based on FBG array inscribed in polyimide-coated multicore optical fiber," Opt. Express 27, 38421-38434 (2019). (Year: 2019).
PCT/US2022/043698 filed Sep. 15, 2022 International Preliminary Report on Patentability dated Mar. 5, 2024.
PCT/US2023/082605 filed Dec. 5, 2023 International Search Report and Written Opinion dated Feb. 28, 2024.
U.S. Appl. No. 17/689,773, filed Mar. 8, 2022 Non-Final Office Action dated Mar. 19, 2024.
U.S. Appl. No. 17/697,895, filed Mar. 17, 2022 Notice of Allowance dated May 8, 2024.
U.S. Appl. No. 17/731,155, filed Apr. 27, 2022 Restriction Requirement dated Feb. 28, 2024.
U.S. Appl. No. 17/849,447, filed Jun. 24, 2022 Non-Final Office Action dated Apr. 10, 2024.
U.S. Appl. No. 17/187,536, filed Feb. 26, 2021 Non-Final Office Action dated Dec. 15, 2023.
U.S. Appl. No. 17/535,406, filed Nov. 24, 2021 Non-Final Office Action dated Feb. 15, 2024.
U.S. Appl. No. 17/697,895, filed Mar. 17, 2022 Non-Final Office Action dated Jan. 11, 2024.
U.S. Appl. No. 17/187,536, filed Feb. 26, 2021 Final Office Action dated Jul. 2, 2024.
U.S. Appl. No. 17/191,551, filed Mar. 3, 2021 Non-Final Office Action dated Aug. 16, 2024.
U.S. Appl. No. 17/535,406, filed Nov. 24, 2021 Final Office Action dated Aug. 1, 2024.
U.S. Appl. No. 17/689,773, filed Mar. 8, 2022 Final Office Action dated Aug. 1, 2024.
U.S. Appl. No. 17/696,675, filed Mar. 16, 2022 Non-Final Office Action dated Jun. 11, 2024.
U.S. Appl. No. 17/725,394, filed Apr. 20, 2022 Non-Final Office Action dated Jun. 17, 2024.
U.S. Appl. No. 17/731,155, filed Apr. 27, 2022 Non-Final Office Action dated Aug. 22, 2024.
U.S. Appl. No. 17/849,447, filed Jun. 24, 2022 Final Office Action dated Aug. 8, 2024.
U.S. Appl. No. 18/524,620, filed Nov. 30, 2023 Non-Final Office Action dated Jun. 18, 2024.
PCT/US2018/026493 filed Apr. 6, 2018 International Search Report and Written Opinion dated Jun. 22, 2018.
PCT/US2020/044801 filed Aug. 3, 2020 International Search Report and Written Opinion dated Oct. 26, 2020.
PCT/US2020/062396 filed Nov. 25, 2020 International Search Report and Written Opinion dated Mar. 2, 2021.
PCT/US2020/062407 filed Nov. 25, 2020 International Search Report and Written Opinion dated Mar. 11, 2021.
PCT/US2021/019713 filed Feb. 25, 2021 International Search Report and Written Opinion dated Jul. 6, 2021.
PCT/US2021/020079 filed Feb. 26, 2021 International Search Report and Written Opinion dated Jun. 4, 2021.
PCT/US2021/020732 filed Mar. 3, 2021 International Search Report and Written Opinion dated Jul. 5, 2021.
PCT/US2021/038954 filed Jun. 24, 2021 International Search Report and Written Opinion dated Oct. 28, 2021.
PCT/US2021/041128 filed Jul. 9, 2021 International Search Report and Written Opinion dated Oct. 25, 2021.
U.S. Appl. No. 15/947,267, filed Apr. 6, 2018 Final Office Action dated Jun. 30, 2021.
U.S. Appl. No. 15/947,267, filed Apr. 6, 2018 Final Office Action dated Nov. 10, 2020.
U.S. Appl. No. 15/947,267, filed Apr. 6, 2018 Non-Final Office Action dated Mar. 12, 2021.
U.S. Appl. No. 15/947,267, filed Apr. 6, 2018 Non-Final Office Action dated May 29, 2020.
U.S. Appl. No. 15/947,267, filed Apr. 6, 2018 Non-Final Office Action dated Oct. 13, 2021.
PCT/US2023/015536 filed Mar. 17, 2023 International Preliminary Report on Patentability dated Sep. 10, 2024.
PCT/US2023/018076 filed Apr. 10, 2023 International Preliminary Report on Patentability dated Oct. 8, 2024.
PCT/US2023/019130 filed Apr. 19, 2023 International Preliminary Report on Patentability dated Oct. 8, 2024.
PCT/US2023/020044 filed Apr. 26, 2023 International Preliminary Report on Patentability dated Oct. 29, 2024.
U.S. Appl. No. 17/187,536, filed Feb. 26, 2021 Advisory Action dated Oct. 9, 2024.
U.S. Appl. No. 17/187,536, filed Feb. 26, 2021 Notice of Allowance dated Oct. 29, 2024.
U.S. Appl. No. 17/191,551, filed Mar. 3, 2021 Notice of Allowance dated Nov. 8, 2024.
U.S. Appl. No. 17/535,406, filed Nov. 24, 2021 Notice of Allowance dated Oct. 23, 2024.
U.S. Appl. No. 17/689,773, filed Mar. 8, 2022 Advisory Action dated Nov. 1, 2024.
U.S. Appl. No. 17/725,394, filed Apr. 20, 2022 Non-Final Office Action dated Nov. 19, 2024.
U.S. Appl. No. 17/849,447, filed Jun. 24, 2022 Advisory Action dated Oct. 24, 2024.
U.S. Appl. No. 17/849,447, filed Jun. 24, 2022 Restriction Requirement dated Apr. 15, 2024.
U.S. Appl. No. 17/863,211, filed Jul. 12, 2022 Restriction Requirement dated Nov. 15, 2024.
U.S. Appl. No. 18/141,289, filed Apr. 28, 2023 Non-Final Office Action dated Sep. 28, 2024.
U.S. Appl. No. 18/524,620, filed Nov. 30, 2023 Notice of Allowance dated Sep. 12, 2024.
U.S. Appl. No. 17/689,773, filed Mar. 8, 2022 Notice of Allowance dated Jan. 15, 2025.
U.S. Appl. No. 17/696,675, filed Mar. 16, 2022 Final Office Action dated Dec. 5, 2024.
U.S. Appl. No. 18/141,289, filed Apr. 28, 2023 Notice of Allowance dated Jan. 10, 2025.
U.S. Appl. No. 18/607,165 filed Mar. 15, 2024 Non-Final Office Action dated Jan. 15, 2025.

* cited by examiner

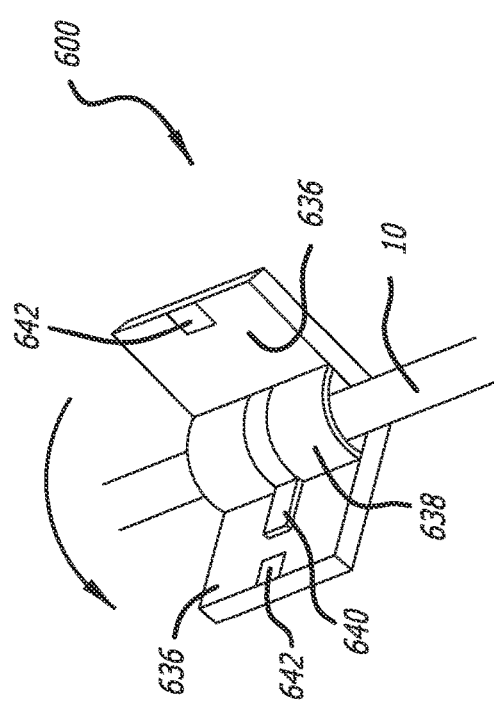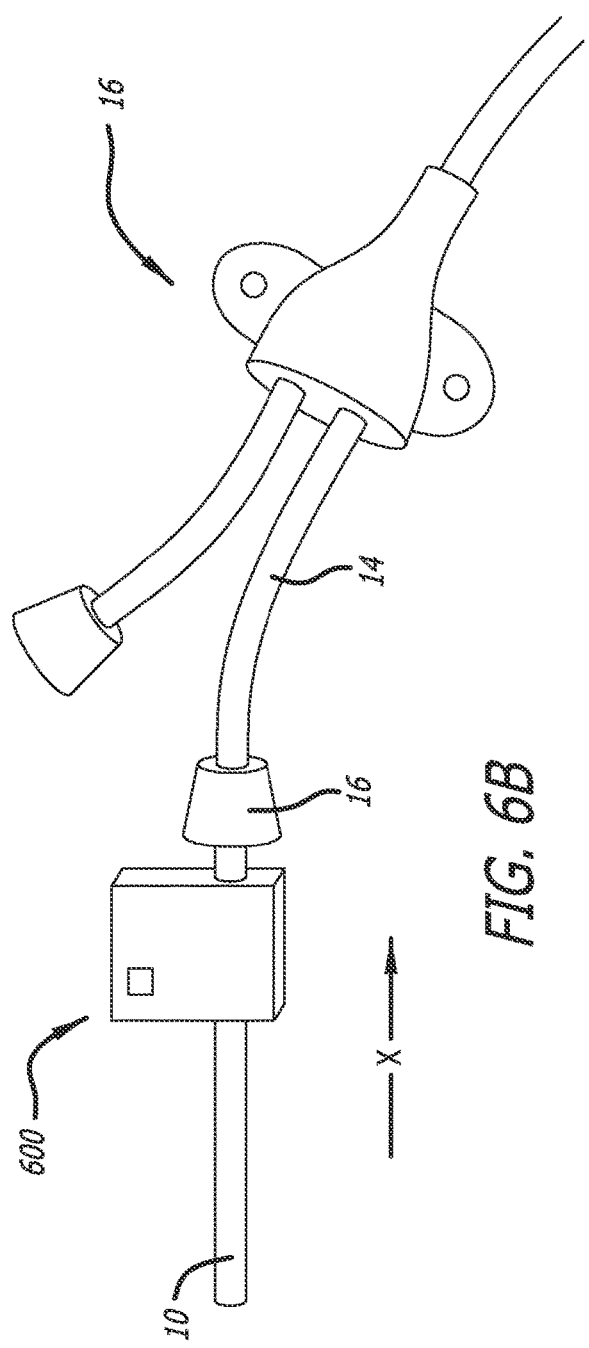
FIG. 6A
FIG. 6B

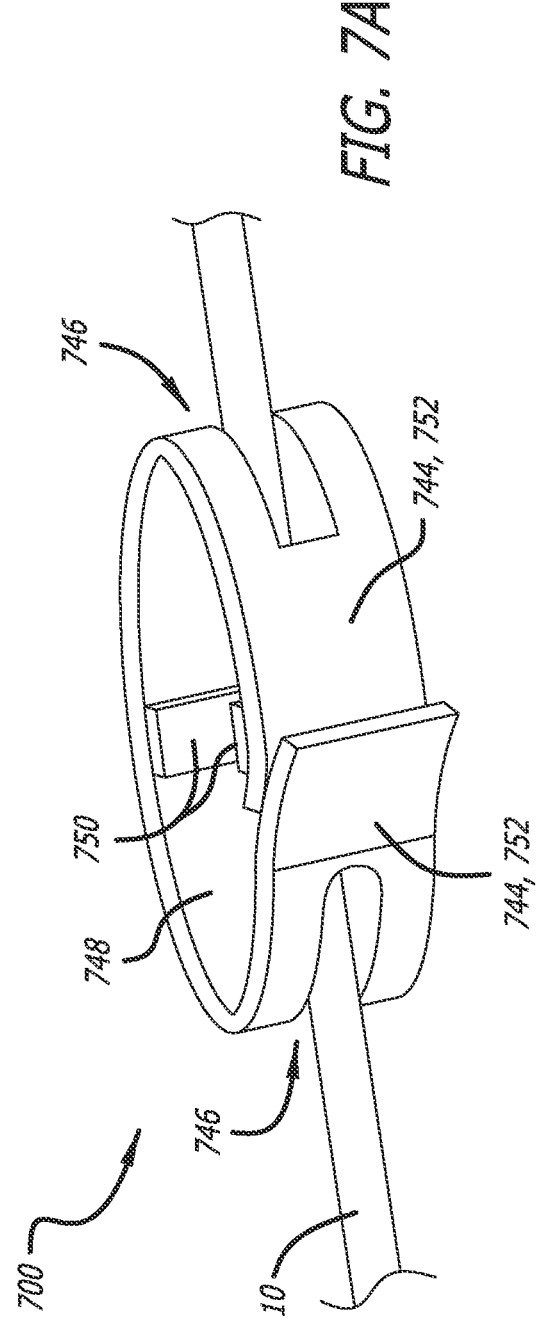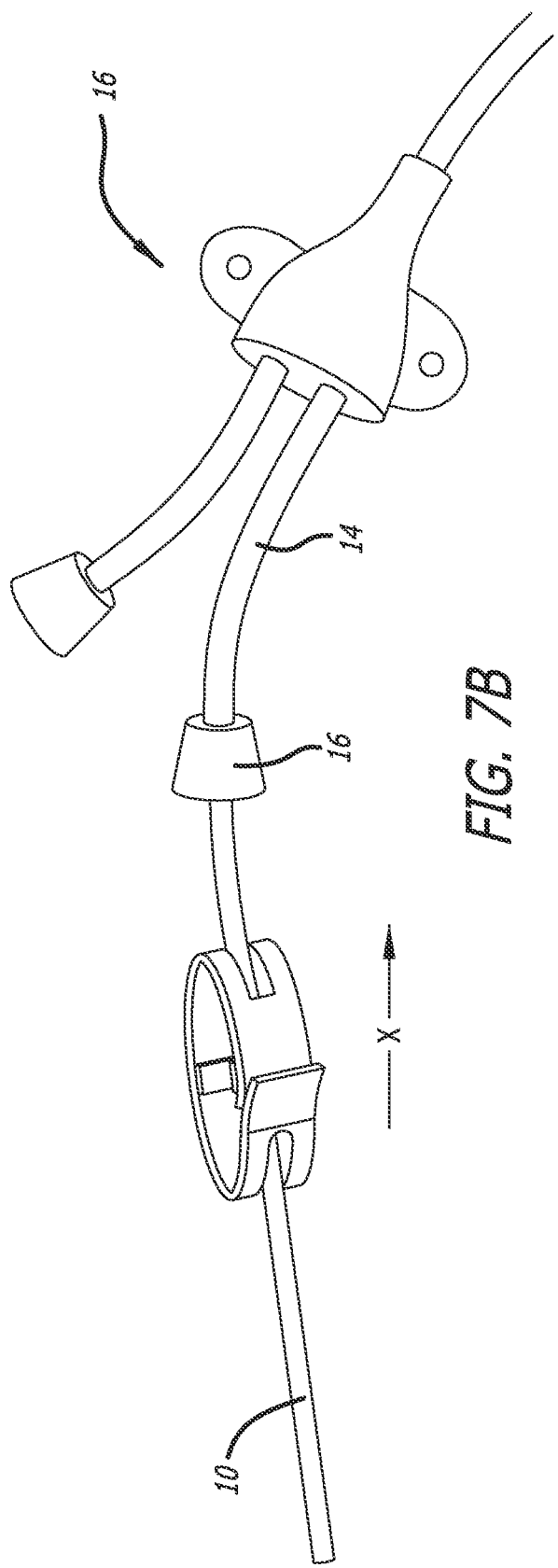

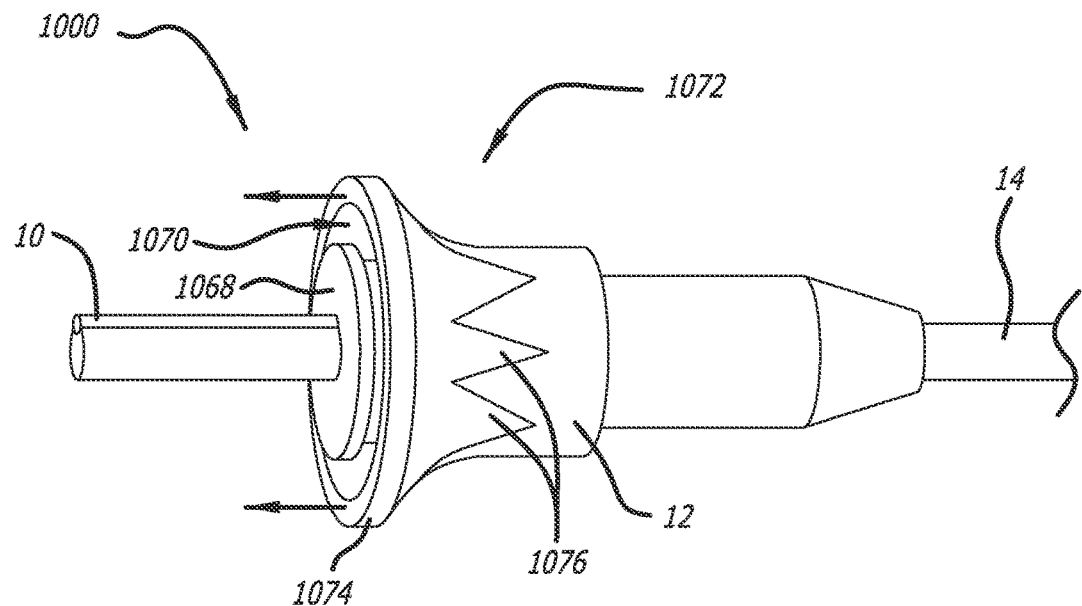
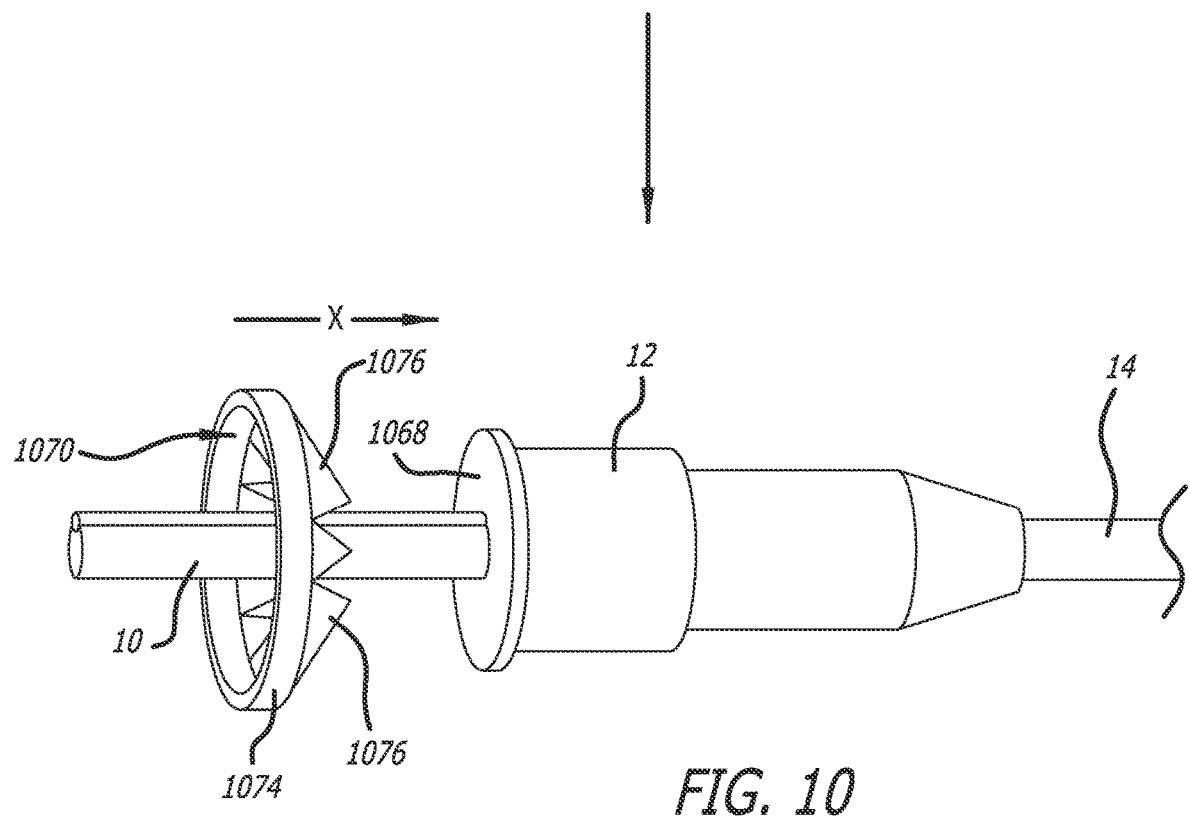
FIG. 10

OPTICAL-FIBER STYLET HOLDERS AND METHODS THEREOF

PRIORITY

This application claims the benefit of priority to U.S. Provisional Patent Application No. 63/115,442, filed Nov. 18, 2020, which is incorporated by reference in its entirety into this application.

BACKGROUND

Intravascular guidance of medical devices including guidewires, catheters, and the like have often used fluoroscopic methods for guiding distal tips of such medical devices through vasculatures and determining whether the distal tips are appropriately placed in their target anatomical locations. However, the fluoroscopic methods expose patients and their attending clinicians to harmful X-ray radiation. Moreover, the patients can be exposed to potentially harmful contrast media needed for the fluoroscopic methods. For these reasons, some current medical research has turned to developing optical methods such has fiberoptic shape-sensing ("FOSS") methods for the intravascular guidance of medical devices.

Current FOSS methods for the intravascular guidance of medical devices utilize optical-fiber stylets having fiber Bragg grating ("FBG") sensors along their length for shape sensing with the optical-fiber stylets. Being made of drawn glass or plastic, such optical-fiber stylets are prone to breakage when folded or "doubled over." However, folding stylets over onto catheters from which the stylets are intravascularly delivered is a common way to hold the stylets in position once their distal tips are appropriately placed in their target anatomical locations. Indeed, FIG. 11 shows how a proximal portion of a stylet 10 extending from a Luer connector 12 is folded over an extension leg 14 of a catheter 16 such as a peripherally inserted central catheter ("PICC") or a central venous catheter ("CVC") to hold the stylet 10 in position. But FIG. 11 also shows how such a stylet can result in breakage if the stylet is an optical-fiber stylet. What is needed is an optical-fiber stylet holder for holding opticalfiber stylets in position in catheters or the like while maintaining functionality of the optical-fiber stylets.

Disclosed herein are optical-fiber stylet holders and methods thereof for holding optical-fiber stylets in position in catheters or the like while maintaining functionality of the optical-fiber stylets.

SUMMARY

Disclosed herein is an optical-fiber stylet holder including, in some embodiments an integrated funnel. The integrated funnel includes a radiused shoulder and a neck. The radiused shoulder has a radius configured to allow an optical-fiber stylet to be placed against the radiused shoulder without breakage of one or more optical fibers in the optical-fiber stylet. The neck has an inner diameter sufficient to accept the optical-fiber stylet, and the neck is configured to be coincident with a lumen of an extension leg of a catheter.

In some embodiments, the optical-fiber stylet holder further includes a locking mechanism. The locking mechanism is configured to lock the optical-fiber stylet in the optical-fiber stylet holder.

In some embodiments, the locking mechanism includes a plurality of notches about a mouth of the integrated funnel through a side wall of the optical-fiber stylet holder. Each notch of the plurality of notches is sized to firmly hold the optical-fiber stylet when the optical-fiber stylet is pressed therein.

In some embodiments, the locking mechanism includes a plurality of side-wall petals about the mouth of the integrated funnel alternating with the plurality of notches. Each side-wall petal of the plurality of side-wall petals is configured to direct the optical-fiber stylet into an adjacent notch when the optical-fiber stylet is pressed thereagainst.

In some embodiments, the locking mechanism includes a cap configured to cover both a mouth of the integrated funnel and the optical-fiber stylet when extending from the mouth. The cap is coupled to a side wall of the optical-fiber stylet holder by a living hinge.

In some embodiments, the optical-fiber stylet holder is integral with a Luer connector of the catheter.

In some embodiments, the optical-fiber stylet holder is a cap including internal threads in a distal portion of the cap configured to screw onto external threads of a Luer connector of the catheter.

Also disclosed herein is an optical-fiber stylet holder including, in some embodiments, a cap, a cylindrical gasket, and a locking mechanism. The cap includes internal threads and a cap through hole. The internal threads are in a distal portion of a bore of the cap, and the internal threads are configured to screw onto complementary external threads of an insertable piece. The cap through hole is in a proximal end of the cap having an inner diameter sufficient to accept an optical-fiber stylet. The cylindrical gasket is of a compressible material. The gasket includes a gasket through hole having an inner diameter no smaller than that of the cap through hole. The locking mechanism is defined by the gasket disposed in the cap between the proximal end of the cap and the insertable piece. The locking mechanism is configured to lock the optical-fiber stylet in the optical-fiber stylet holder by compression of the gasket when the cap is screwed onto the insertable piece with the optical-fiber stylet in the optical-fiber stylet holder.

In some embodiments, the compression of the gasket is axial compression between the proximal end of the cap and the insertable piece. The axial compression, in turn, provides radial compression around the optical-fiber stylet to lock the optical-fiber stylet in the optical-fiber stylet holder.

In some embodiments, the insertable piece is part of a male Luer connector of a catheter.

In some embodiments, the insertable piece is part of the optical-fiber stylet holder. The insertable piece has a distal portion configured as a female Luer connector.

Also disclosed herein is an optical-fiber stylet holder including, in some embodiments, a pair of arms, a tortuous path for an optical-fiber stylet to follow between the pair of arms, and a locking mechanism. The pair of arms is biased toward a centerline of the optical-fiber stylet holder. The locking mechanism is defined by the torturous path. The locking mechanism is configured to lock the optical-fiber stylet in the optical-fiber stylet holder by friction through a combination of the pair of arms being biased toward the centerline of the optical-fiber stylet holder and the tortuous path formed between the pair of arms.

In some embodiments, the optical-fiber stylet further includes a plurality of rollers mounted on the pair of arms. Consecutive rollers of the plurality of rollers alternate from arm to arm of the pair of arms forming a tortuous path for an optical-fiber stylet to follow.

In some embodiments, the optical-fiber stylet holder is integral with a Luer connector of the catheter.

In some embodiments, the optical-fiber stylet holder is a cap including internal threads in a distal portion of the cap configured to screw onto external threads of a Luer connector of the catheter.

Also disclosed herein is an optical-fiber stylet holder including, in some embodiments, a clamp, a through hole through a distal end of the optical-fiber stylet holder coincident with a lumen of an extension leg of a catheter, and a locking mechanism defined by the clamp. The clamp includes a first jaw, a second jaw, and an elastic piece configured to store mechanical energy. The first jaw and the second jaw longitudinally extend in a same direction as that of a centerline of the optical-fiber stylet holder. The elastic piece is coupled to both the first jaw and the second jaw, and the elastic piece is configured to hold the second jaw against the first j aw. The locking mechanism is configured to lock the optical-fiber stylet in the optical-fiber stylet holder by friction of the clamp along a length of the optical-fiber stylet.

In some embodiments, the optical-fiber stylet holder is integral with a Luer connector of the catheter.

In some embodiments, the optical-fiber stylet holder is a cap including internal threads in a distal portion of the cap configured to screw onto external threads of a Luer connector of the catheter.

Also disclosed herein is an optical-fiber stylet holder including, in some embodiments, a pair of hinge plates, a hinge formed between the pair of hinge plates, and an elastomeric pad disposed on a hinge plate of the pair of hinge plates. Each hinge plate of the pair of hinge plates includes a fastener complementary to the other. The hinge formed between the pair of hinge plates utilizes an optical-fiber stylet to provide a hinge pin of the hinge. The elastomeric pad is configured to compress the optical-fiber stylet against another hinge plate of the pair of hinge plates when the pair of hinge plates are closed. The optical-fiber stylet holder thereby provides a locking mechanism configured to lock the optical-fiber stylet in the optical-fiber stylet holder and prevent distal movement of the optical-fiber stylet while the optical-fiber stylet is disposed in a catheter.

In some embodiments, the optical-fiber stylet holder is configured to couple to a Luer connector of the catheter.

Also disclosed herein is an optical-fiber stylet holder including, in some embodiments, a pair of arms, a pair of opposing through holes, a connecting portion between the pair of arms, and a pair of opposing elastomeric pads. The pair of arms includes a stationary arm and a moveable arm. Each arm of the pair of arms includes a fastener complementary to the other. Each through hole of the pair of through holes is through at least an arm of the pair of arms. An elastomeric pad of the pair of elastomeric pads is disposed on the moveable arm and another elastomeric pad of the pair of elastomeric pads is disposed on the connecting portion. The pair of elastomeric pads are configured to compress an optical-fiber stylet inserted through the through holes when the moveable arm is moved toward the connecting portion. The optical-fiber stylet holder thereby provides a locking mechanism configured to lock the optical-fiber stylet in the optical-fiber stylet holder and prevent distal movement of the optical-fiber stylet while the optical-fiber stylet is disposed in a catheter.

In some embodiments, the stationary arm includes a rack of teeth and the moveable arm includes a pawl. The pawl is configured to move linearly across the rack of teeth as the moveable arm is moved toward the connecting portion.

In some embodiments, the optical-fiber stylet holder is configured to couple to a Luer connector of the catheter.

Also disclosed herein is an optical-fiber stylet holder including, in some embodiments, a housing, an insert, and a spring. The housing includes a housing through hole dimensioned to accept an optical-fiber stylet therethrough. The insert is partially disposed in the housing and partially extends as a button from a side of the housing perpendicular to the housing through hole. The insert includes an insert through hole coincident with the housing through hole. The spring is configured to push or pull the insert toward the side of the housing from which the insert extends. The optical-fiber stylet acts as a stop to the insert being pushed or pulled toward the side of the housing when the optical-fiber stylet is inserted through both the housing through hole and the insert through hole. The optical-fiber stylet holder thereby provides a locking mechanism configured to lock the optical-fiber stylet in the optical-fiber stylet holder and prevent distal movement of the optical-fiber stylet while the optical-fiber stylet is disposed in a catheter.

In some embodiments, the optical-fiber stylet holder is configured to couple to a Luer connector of the catheter.

Also disclosed herein is an optical-fiber stylet holder including, in some embodiments, a substrate and a torturous channel in a side of the substrate. The torturous channel is dimensioned to accept an optical-fiber stylet laid therein. The optical-fiber stylet holder thereby provides a locking mechanism configured to lock the optical-fiber stylet in the optical-fiber stylet holder and prevent distal movement of the optical-fiber stylet while the optical-fiber stylet is disposed in a catheter.

In some embodiments, the optical-fiber stylet holder is configured to couple to a Luer connector of the catheter.

Also disclosed herein is an optical-fiber stylet holder including, in some embodiments, a septum configured to be disposed in a Luer connector of a catheter. The septum includes a through hole dimensioned to accept an optical-fiber stylet therethrough and firmly hold the optical-fiber stylet by friction when the optical-fiber stylet is inserted therein. The optical-fiber stylet holder thereby provides a locking mechanism configured to lock the optical-fiber stylet in the optical-fiber stylet holder and prevent both proximal and distal movement of the optical-fiber stylet while the optical-fiber stylet is disposed in a catheter.

In some embodiments, the optical-fiber stylet holder further includes a retainer. The retainer includes an annular rim and a plurality of wedge-shaped pieces extending from the rim and biased toward a center of the retainer. The retainer is configured to slide off the Luer connector and onto the optical-fiber stylet bringing tips of the wedge-shaped pieces inward toward the center of the retainer.

In some embodiments, the retainer provides a secondary locking mechanism configured to prevent distal movement of the optical-fiber stylet while the optical-fiber stylet is disposed in a catheter.

Also disclosed herein is a method of an optical-fiber stylet holder including, in some embodiments, a stylet-inserting step, a first stylet-advancing step, a second stylet-advancing step, and a stylet-holding step. The stylet-inserting step includes inserting an optical-fiber stylet into the optical-fiber stylet holder. The first stylet-advancing step includes advancing the optical-fiber stylet through a catheter. The second stylet-advancing step includes advancing a distal tip of the optical-fiber stylet through a vasculature to a target anatomical location in a patient. The stylet-holding step includes holding the distal tip of the optical-fiber stylet in the target anatomical location without at least distal advancement of the distal tip by locking the optical-fiber stylet in the optical-fiber stylet holder.

In some embodiments, the method further includes a stylet-placing step, a first stylet-pressing step, and a second stylet-pressing step. The stylet-placing step includes placing the optical-fiber stylet against a radiused shoulder of an integrated funnel of the optical-fiber stylet holder. The first stylet-pressing step includes pressing the optical-fiber stylet against a side-wall petal of a plurality of side-wall petals about a mouth of the integrated funnel to direct the optical-fiber stylet into an adjacent notch of a plurality of notches about the mouth of the integrated funnel. The second stylet-pressing step includes pressing the optical-fiber stylet into a notch of the plurality of notches, thereby locking the optical-fiber stylet in the optical-fiber stylet holder and holding the distal tip of the optical-fiber stylet in the target anatomical location.

In some embodiments, the method further includes the stylet-placing step and a mouth-covering step. Again, the stylet-placing step includes placing the optical-fiber stylet against a radiused shoulder of an integrated funnel of the optical-fiber stylet holder. The mouth-covering step includes covering a mouth of the integrated funnel with a cap coupled to a side wall of the optical-fiber stylet holder by a living hinge, thereby locking the optical-fiber stylet in the optical-fiber stylet holder and holding the distal tip of the optical-fiber stylet in the target anatomical location.

In some embodiments, the method further includes a cap-screwing step and a compressing step. The cap-screwing step includes screwing a cap of the optical-fiber stylet holder onto an insertable piece. The compressing step includes compressing around the optical-fiber stylet a cylindrical gasket disposed in the cap between a proximal end of the cap and the insertable piece with the screwing of the cap onto the insertable piece, thereby locking the optical-fiber stylet in the optical-fiber stylet holder and holding the distal tip of the optical-fiber stylet in the target anatomical location.

In some embodiments, the stylet-inserting step includes following a torturous path with the optical fiber stylet through a plurality of rollers mounted on a pair of arms biased toward a centerline of the optical-fiber stylet holder, thereby locking the optical-fiber stylet in the optical-fiber stylet holder and holding the distal tip of the optical-fiber stylet in the target anatomical location.

In some embodiments, the method further includes a clamp-opening step and a clamp-closing step. The clamp-opening step includes opening a clamp of the optical-fiber stylet holder before the stylet-inserting step. The clamp-closing step includes closing a second jaw of the clamp onto a first jaw of the clamp with the optical-fiber stylet between the second jaw and the first jaw, thereby locking the optical-fiber stylet in the optical-fiber stylet holder and holding the distal tip of the optical-fiber stylet in the target anatomical location.

In some embodiments, the method further includes a hinge-closing step. The hinge-closing step includes closing a pair of hinge plates of the optical-fiber stylet holder to compress the optical-fiber stylet with an elastomeric pad of a hinge plate of the pair of hinge plates against another hinge plate of the pair of hinge plates, thereby locking the optical-fiber stylet in the optical-fiber stylet holder and holding the distal tip of the optical-fiber stylet in the target anatomical location.

In some embodiments, the stylet-inserting step includes inserting the optical-fiber stylet into a pair of opposing through holes through a pair of arms including a stationary arm and a moveable arm.

In some embodiments, the method further includes a pawl-moving step. The pawl-moving step includes moving a pawl of the moveable arm against a rack of teeth of the stationary arm to compress the optical-fiber stylet between an elastomeric pad disposed on the moveable arm and another elastomeric pad disposed on a connecting portion of the optical-fiber stylet holder between the pair of arms, thereby locking the optical-fiber stylet in the optical-fiber stylet holder and holding the distal tip of the optical-fiber stylet in the target anatomical location.

In some embodiments, the method further includes a button-pressing step and a button-releasing step. The button-pressing step includes pressing a button of an insert extending from a side of a housing of the optical-fiber stylet holder to pull or push a spring to allow the optical-fiber stylet to freely move through both housing and insert through holes for adjusting a position of the optical-fiber stylet holder on the optical-fiber stylet. The button-releasing step includes releasing the button to push or pull the insert by way of the spring toward the side of the housing from which the insert extends, thereby locking the optical-fiber stylet in the optical-fiber stylet holder as a stop in the housing and insert through holes and holding the distal tip of the optical-fiber stylet in the target anatomical location.

In some embodiments, the stylet-inserting step includes laying the optical-fiber stylet into a torturous channel in a side of a substrate of the optical-fiber stylet holder, thereby locking the optical-fiber stylet in the optical-fiber stylet holder and holding the distal tip of the optical-fiber stylet in the target anatomical location.

In some embodiments, the stylet-inserting step includes inserting the optical-fiber stylet into a through hole of a septum of the optical-fiber stylet holder, thereby locking the optical-fiber stylet in the optical-fiber stylet holder by friction and holding the distal tip of the optical-fiber stylet in the target anatomical location.

These and other features of the concepts provided herein will become more apparent to those of skill in the art in view of the accompanying drawings and following description, which describe particular embodiments of such concepts in greater detail.

DRAWINGS

FIG. 6A illustrates a sixth optical-fiber stylet holder in accordance with some embodiments.

FIG. 6B illustrates the sixth optical-fiber stylet holder in use with a catheter in accordance with some embodiments.

FIG. 7A illustrates a seventh optical-fiber stylet holder in accordance with some embodiments.

FIG. 7B illustrates the seventh optical-fiber stylet holder in use with catheter in accordance with some embodiments.

FIG. 10 illustrates a tenth optical-fiber stylet holder in accordance with some embodiments.

DESCRIPTION

Figure 1:
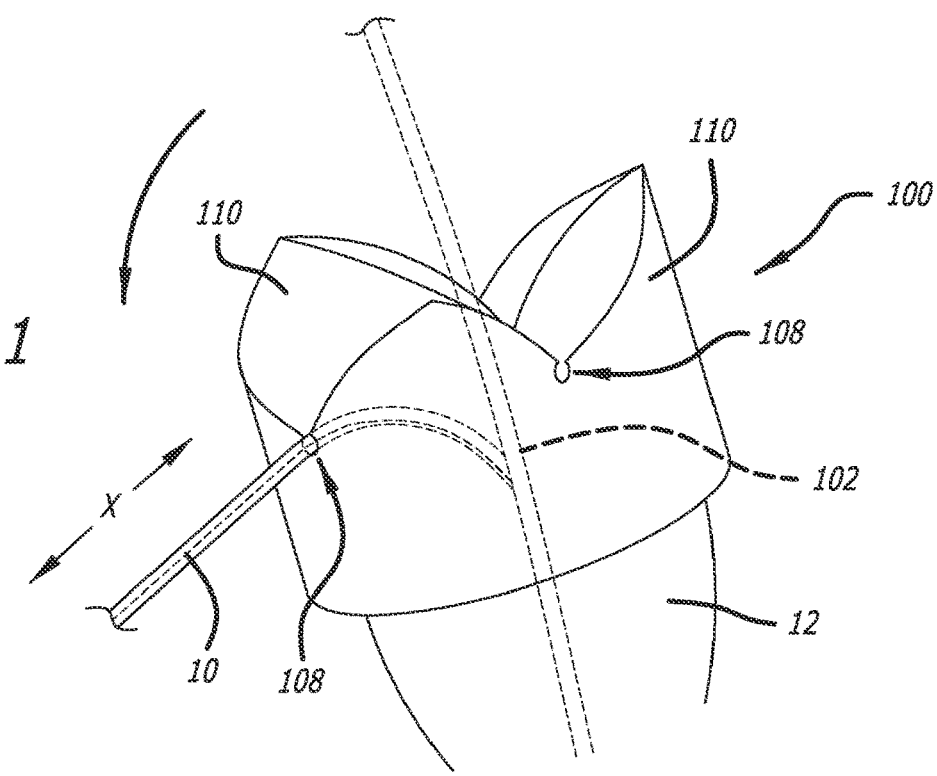
FIG. 1 illustrates a first optical-fiber stylet holder in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

Figure 11:
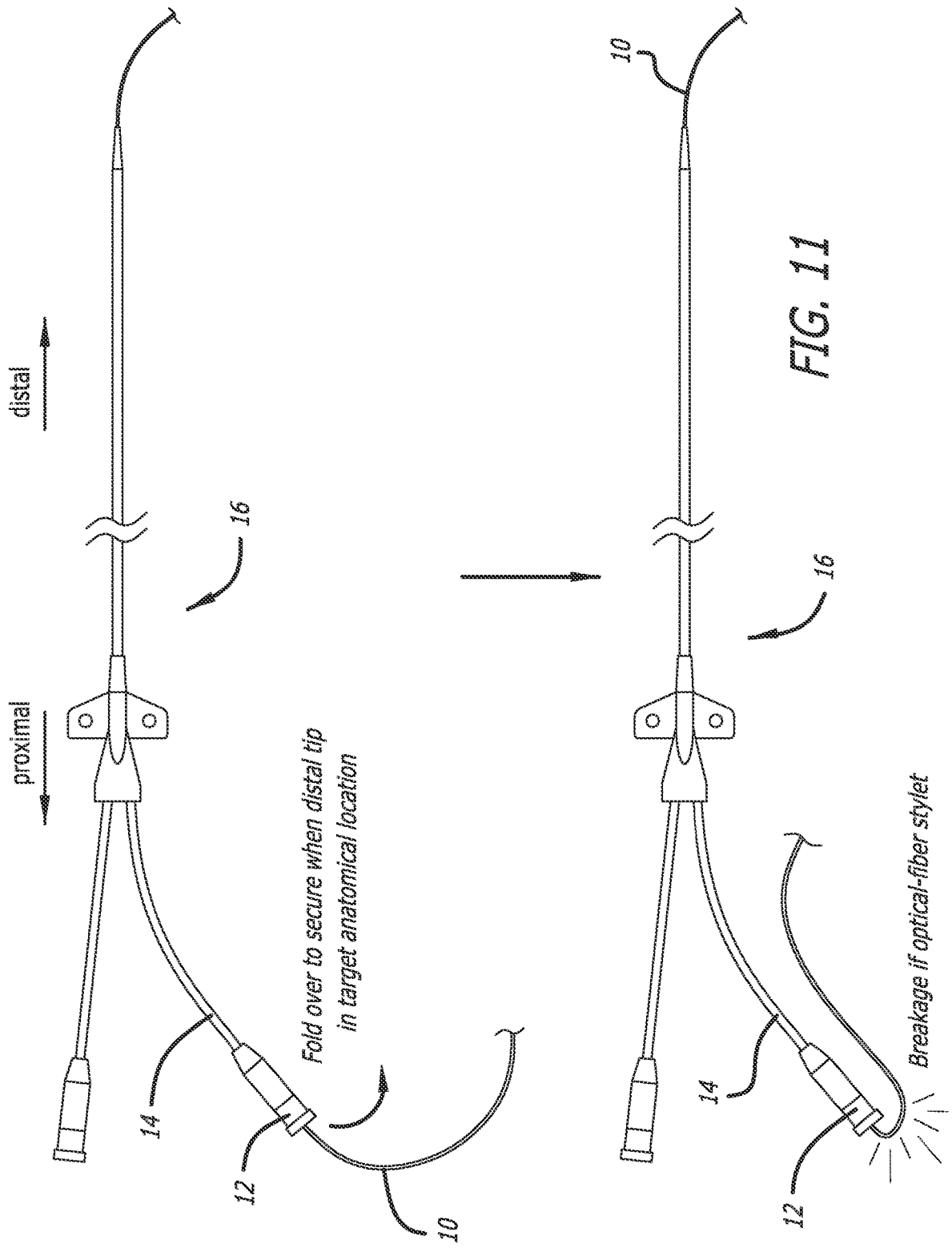
FIG. 11 illustrates a common way to hold stylets in position once their distal tips are appropriately placed in their target anatomical locations, which way is unsuitable for optical-fiber stylets.

As set forth above, folding stylets over onto catheters from which the stylets are intravascularly delivered is a common way to hold the stylets in position once their distal tips are appropriately placed in their target anatomical locations. Indeed, FIG. 11 shows how the proximal portion of the stylet 10 extending from the Luer connector 12 is folded over the extension leg 14 of the catheter 16 such as a PICC or a CVC to hold the stylet 10 in position. But FIG. 11 also shows how such a stylet can result in breakage if the stylet is an optical-fiber stylet drawn from glass or plastic. What is needed is an optical-fiber stylet holder for holding optical-fiber stylets in position in catheters or the like while maintaining functionality of the optical-fiber stylets. Disclosed herein are optical-fiber stylet holders and methods thereof for holding optical-fiber stylets in position in catheters or the like while maintaining functionality of the optical-fiber stylets.

Figure 2:
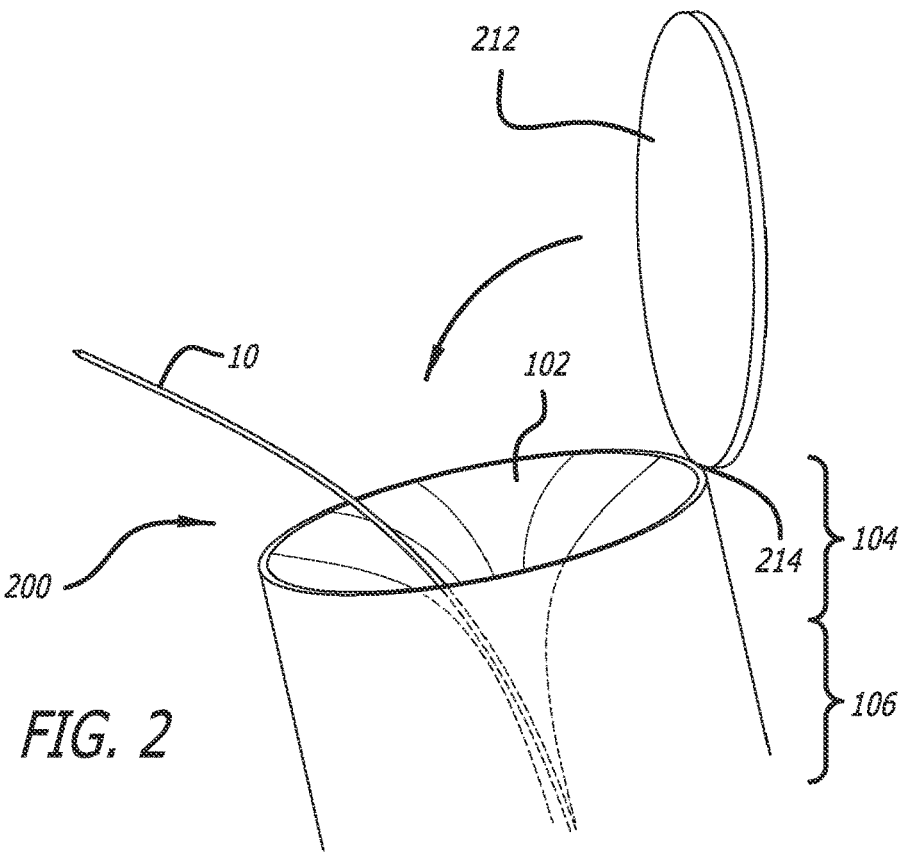
FIG. 2 illustrates a second optical-fiber stylet holder in accordance with some embodiments.

FIGS. 1 and 2 respectively illustrate a first optical-fiber stylet holder 100 and a second optical-fiber stylet holder 200 in accordance with some embodiments.

As shown, the optical-fiber stylet holder 100 or 200 includes an integrated funnel 102 and a locking mechanism configured to lock an optical-fiber stylet such as the optical-fiber stylet 10 in the optical-fiber stylet holder 100 or 200, thereby preventing proximal or distal movement of the optical-fiber stylet 10.

The integrated funnel 102 includes a radiused shoulder 104 and a neck 106. The radiused shoulder 104 has a radius configured to allow the optical-fiber stylet 10 to be placed against the radiused shoulder 104 without breakage of one or more optical fibers in the optical-fiber stylet 10. Advantageously, the radius of the radiused shoulder 104, being known, can be used for FOSS system calibration. The neck 106 has an inner diameter sufficient to accept the optical-fiber stylet 10. The neck is configured to be coincident with a lumen of an extension leg of a catheter such as the extension leg 14 of the catheter 16 for advancing the optical-fiber stylet 10 through the catheter 16. The integrated funnel 102 can be formed of a semi-flexible material.

As shown in FIG. 1, the locking mechanism can include a plurality of notches 108 about a mouth of the integrated funnel 102 through a side wall of the optical-fiber stylet holder 100. Each notch of the plurality of notches 108 is sized to firmly hold the optical-fiber stylet 10 when the optical-fiber stylet 10 is pressed therein. In addition, the locking mechanism can include a plurality of side-wall petals 110 about the mouth of the integrated funnel 102 alternating with the plurality of notches 108. Each side-wall petal of the plurality of side-wall petals 110 is configured to direct the optical-fiber stylet 10 into an adjacent notch when the optical-fiber stylet is pressed thereagainst.

As shown in FIG. 2, the locking mechanism includes a cap 212 configured to cover both a mouth of the integrated funnel 102 and the optical-fiber stylet 10 when the optical-fiber stylet 10 extends from the mouth. The cap 212 is coupled to a side wall of the optical-fiber stylet holder 200 by a living hinge 214.

The optical-fiber stylet holder 100 or 200 can be integral with the Luer connector 12 of the catheter 16. Alternatively, the optical-fiber stylet holder 100 or 200 is a cap including internal threads in a distal portion of the cap configured to screw onto external threads of the Luer connector 12 of the catheter 16. Since Luer connectors are standardized, the latter embodiment is advantageous in that the optical-fiber stylet holder 100 or 200 can be used with existing PICCs, CVC, or the like.

Figure 3:
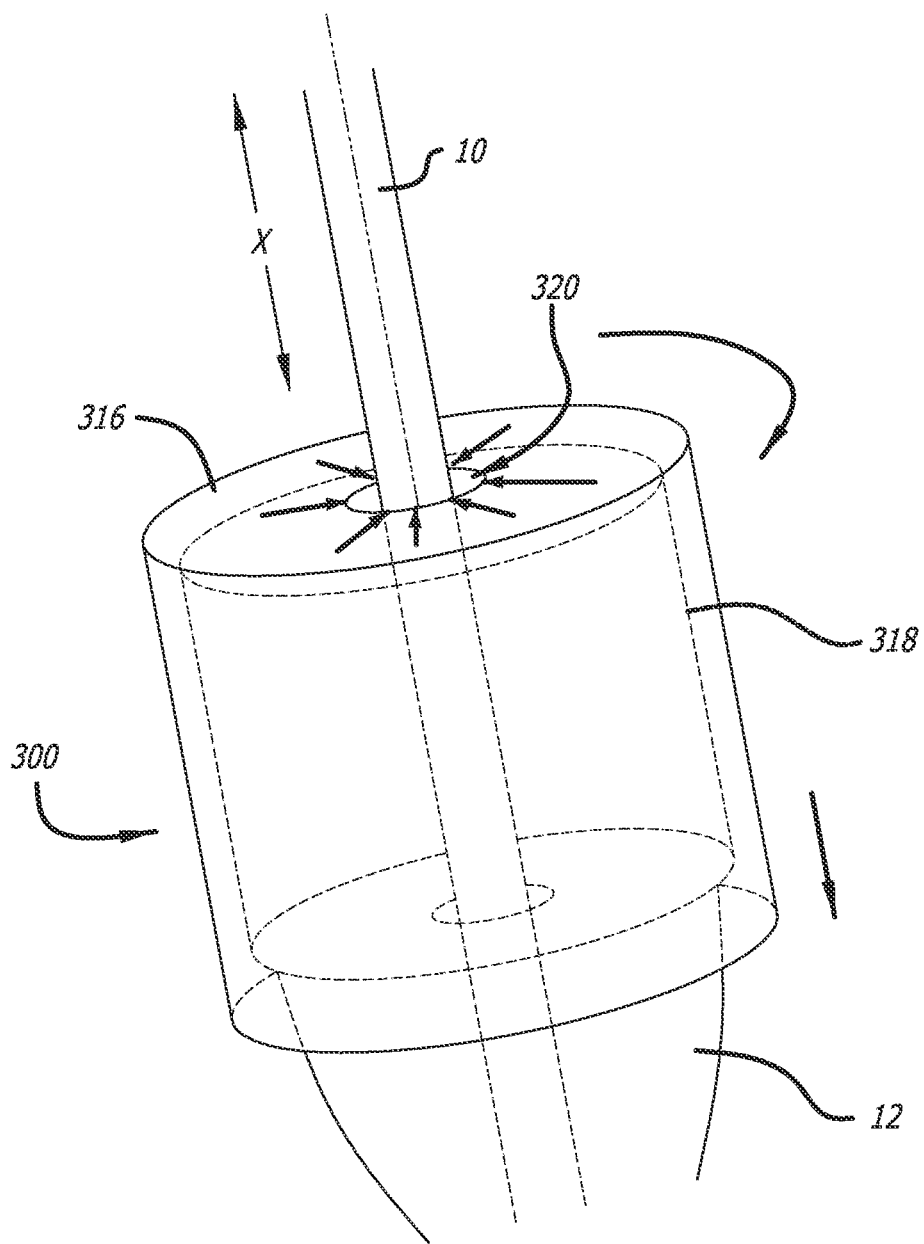
FIG. 3 illustrates a third optical-fiber stylet holder in accordance with some embodiments.

FIG. 3 illustrates a third optical-fiber stylet holder 300 in accordance with some embodiments.

As shown, the optical-fiber stylet holder 300 includes a cap 316, a cylindrical gasket 318, and a locking mechanism configured to lock an optical-fiber stylet such as the optical-fiber stylet 10 in the optical-fiber stylet holder 300, thereby preventing proximal or distal movement of the optical-fiber stylet 10.

The cap includes internal threads (not shown) and a cap through hole 320. The internal threads are in a distal portion of a bore of the cap 316. The internal threads are configured to screw onto complementary external threads of an insertable piece. The cap through hole 320 is in a proximal end of the cap 316. The cap through hole 320 has an inner diameter sufficient to accept the optical-fiber stylet 10 inserted therein.

The gasket 318 is of a compressible material such as an elastomeric material. The gasket 318 includes a gasket through hole (not shown) having an inner diameter no smaller than that of the cap through hole 320. The gasket through hole is configured to be coincident with a lumen of an extension leg of a catheter such as the extension leg 14 of the catheter 16 for advancing the optical-fiber stylet 10 through the catheter 16.

The locking mechanism is defined by the gasket 318 disposed in the cap 316 between the proximal end of the cap 316 and the insertable piece. The locking mechanism is configured to lock the optical-fiber stylet 10 in the optical-fiber stylet holder 300 by compression of the gasket 318 when the cap 316 is screwed onto the insertable piece with the optical-fiber stylet 10 in the optical-fiber stylet holder 300. The compression of the gasket 318 is axial compression between the proximal end of the cap 316 and the insertable piece. The axial compression, in turn, provides radial compression around the optical-fiber stylet 10 to lock the optical-fiber stylet 10 in the optical-fiber stylet holder 300.

The insertable piece can be a part (e.g., a proximal portion) of the Luer connector 12 of the catheter 16, which Luer connector 12 is a male Luer connector having external threads. Alternatively, the insertable piece is part of the optical-fiber stylet holder 300. In the latter embodiment, the insertable piece can have a distal portion configured as a female Luer connector having internal threads complementary to the external threads of the Luer connector 12 and a proximal portion with the external threads complementary to the internal threads of the cap 316. The insertable piece as part of the optical-fiber stylet holder 300 is advantageous in that the thread pitch does not have to match that specified for Luer connectors, which are not necessarily designed for finer-tuned movements such as those beneficial for compressing the optical-fiber stylet 10 in the optical-fiber stylet holder 300.

Figure 4:
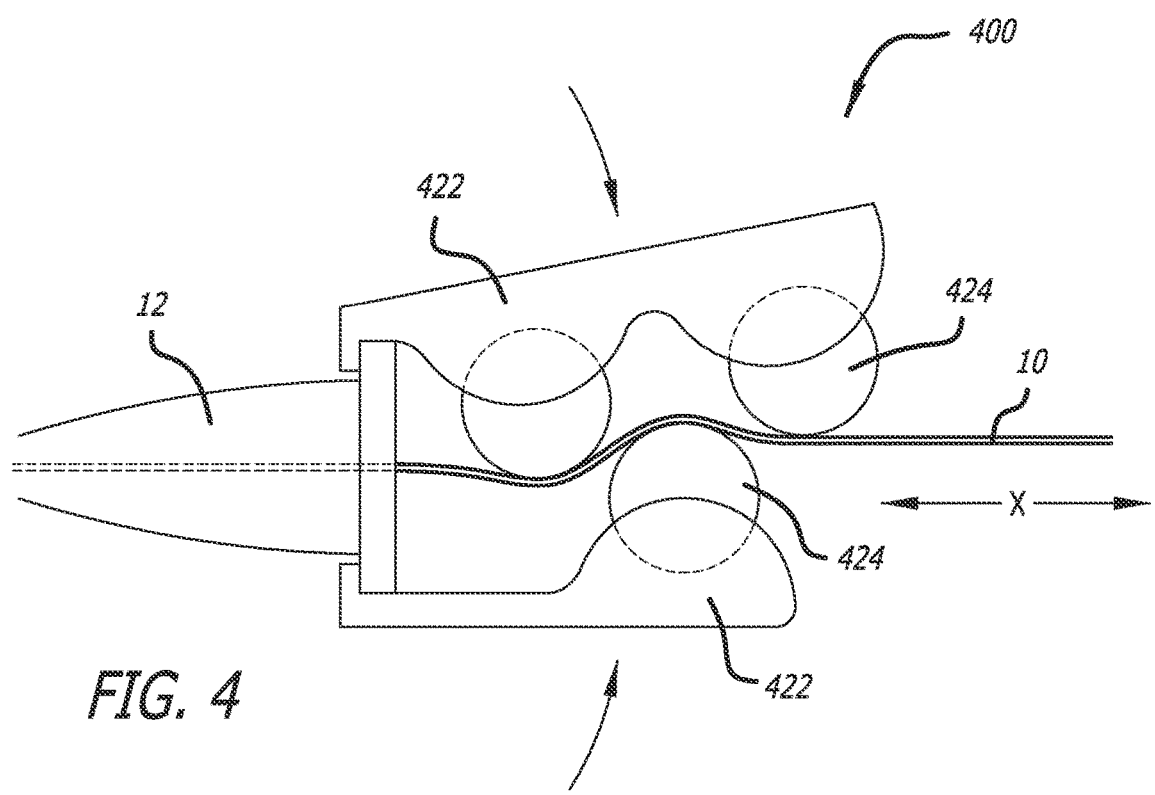
FIG. 4 illustrates a fourth optical-fiber stylet holder in accordance with some embodiments.

FIG. 4 illustrates a fourth optical-fiber stylet holder 400 in accordance with some embodiments.

As shown, the optical-fiber stylet holder 400 includes a pair of arms 422, a plurality of rollers 424 mounted on the pair of arms 422, and a locking mechanism configured to lock an optical-fiber stylet such as the optical-fiber stylet 10 in the optical-fiber stylet holder 400, thereby preventing proximal or distal movement of the optical-fiber stylet 10.

The pair of arms 422 is biased toward a centerline of the optical-fiber stylet holder 400. The plurality of rollers 424 is mounted on the pair of arms 422. Consecutive rollers of the plurality of rollers 424 alternate from arm to arm of the pair of arms 422 forming a tortuous path for the optical-fiber stylet 10 to follow. Advantageously, the torturous path, being known, can be used for FOSS system calibration.

The optical-fiber stylet holder 400 also includes a distal through hole distal of the plurality of rollers 424 and through a distal end of the optical-fiber stylet holder 400, which through hole is coincident with a lumen of an extension leg of a catheter such as the extension leg 14 of the catheter 16 for advancing the optical-fiber stylet 10 through the catheter 16.

The locking mechanism is defined by the plurality of rollers 424 mounted on the pair of arms 422. The locking mechanism is configured to lock the optical-fiber stylet 10 in the optical-fiber stylet holder 400 by friction through a combination of the pair of arms 422 being biased toward the centerline of the optical-fiber stylet holder 400 and the tortuous path formed by the plurality of rollers 424.

The optical-fiber stylet holder 400 can be integral with the Luer connector 12 of the catheter 16. Alternatively, the optical-fiber stylet holder 400 is a cap including internal threads in a distal portion of the cap configured to screw onto external threads of the Luer connector 12 of the catheter 16. Since Luer connectors are standardized, the latter embodiment is advantageous in that the optical-fiber stylet holder 400 can be used with existing PICCs, CVC, or the like.

Figure 5:
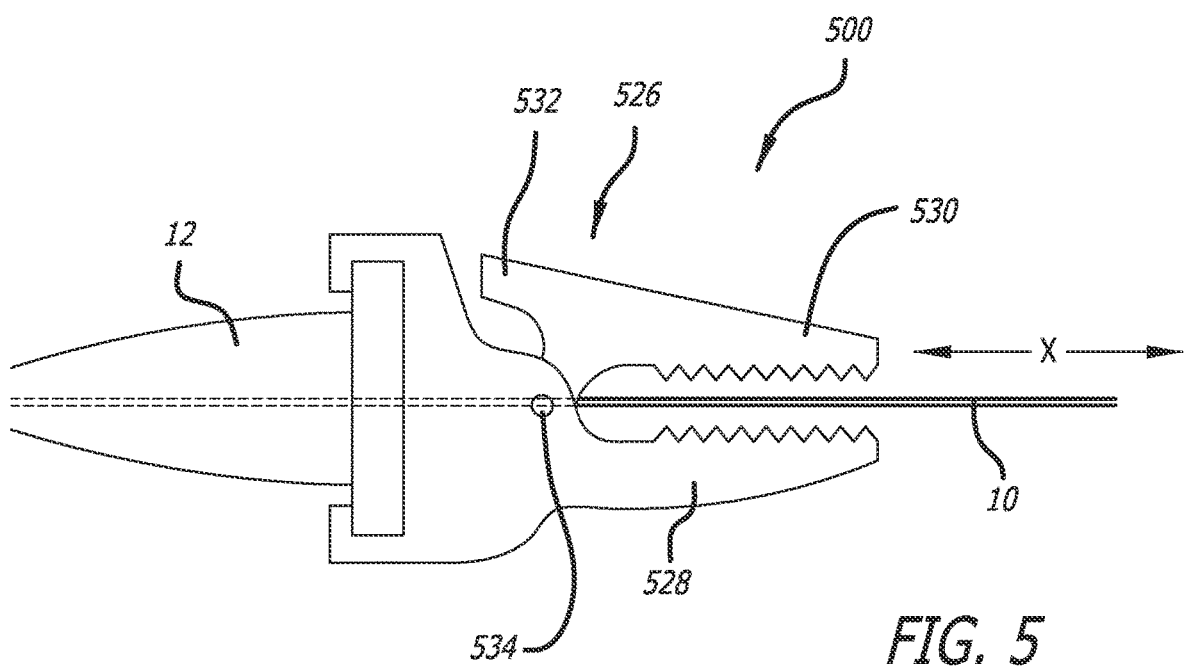
FIG. 5 illustrates a fifth optical-fiber stylet holder in accordance with some embodiments.

FIG. 5 illustrates a fifth optical-fiber stylet holder 500 in accordance with some embodiments.

As shown, the optical-fiber stylet holder 500 includes a clamp 526, a through hole through a distal end of the optical-fiber stylet holder 500 coincident with a lumen of an extension leg of a catheter such as the extension leg 14 of the catheter 16, and a locking mechanism defined by the clamp 526 configured to lock an optical-fiber stylet such as the optical-fiber stylet 10 in the optical-fiber stylet holder 500, thereby preventing proximal or distal movement of the optical-fiber stylet 10.

The clamp includes a first jaw 528 such as a stationary jaw, a second jaw 530 such as a moveable jaw, and an elastic piece (e.g., a metal spring, a molded plastic piece having a bias toward each side of the molded plastic piece, etc.) configured to store mechanical energy (not shown). The first jaw 528 and the second jaw 530 longitudinally extend in a same direction as that of a centerline of the optical-fiber stylet holder 500. The elastic piece is coupled to both the first jaw 528 and the second jaw 530, and the elastic piece is configured to hold the second jaw 530 against the first jaw 528 or vice versa. Indeed, both the first jaw 528 and the second jaw 530 can be moveable from a common anchor point of the optical-fiber stylet holder 500. A thumb pad 532 is configured to allow a clinician to press into the clamp 526 with his or her thumb on an opposite side of a hinge pin 534 to overcome a elastic-piece force of the elastic piece holding the second jaw 530 against the first jaw 528, thereby allowing adjustment (e.g., proximal or distal movement) of the optical fiber stylet 10.

The locking mechanism is configured to lock the optical-fiber stylet 10 in the optical-fiber stylet holder 500 by friction of the clamp 526 along a length of the optical-fiber stylet 10.

The optical-fiber stylet holder 500 can be integral with the Luer connector 12 of the catheter 16. Alternatively, the optical-fiber stylet holder 500 is a cap including internal threads in a distal portion of the cap configured to screw onto external threads of the Luer connector 12 of the catheter 16. Since Luer connectors are standardized, the latter embodiment is advantageous in that the optical-fiber stylet holder 500 can be used with existing PICCs, CVC, or the like.

FIG. 6A illustrates a sixth optical-fiber stylet holder 600 in accordance with some embodiments. FIG. 6B illustrates the sixth optical-fiber stylet holder 600 in use with a catheter in accordance with some embodiments.

As shown, the optical-fiber stylet holder 600 includes a pair of hinge plates 636, a hinge 638 formed between the pair of hinge plates 636, and an elastomeric pad 640 disposed on a hinge plate of the pair of hinge plates 636.

Each hinge plate of the pair of hinge plates 636 includes a fastener complementary to the other making a pair of fasteners 642.

The hinge 638 formed between the pair of hinge plates 636 utilizes an optical-fiber stylet such as the optical-fiber stylet 10 to provide a hinge pin of the hinge 638.

The elastomeric pad 640 is configured to compress the optical-fiber stylet 10 against another hinge plate of the pair of hinge plates 636 when the pair of hinge plates 636 are closed.

The optical-fiber stylet holder 600 thereby provides a locking mechanism configured to lock the optical-fiber stylet 10 in the optical-fiber stylet holder 600 and prevent distal movement of the optical-fiber stylet 10 while the optical-fiber stylet 10 is disposed in a catheter such as the catheter 16. However, the optical-fiber stylet holder 600 can be configured to couple to a Luer connector of the catheter 16 to prevent proximal movement of the optical-fiber stylet 10 as well.

FIG. 7A illustrates a seventh optical-fiber stylet holder 700 in accordance with some embodiments. FIG. 7B illustrates the seventh optical-fiber stylet holder 700 in use with catheter in accordance with some embodiments.

As shown, the optical-fiber stylet holder 700 includes a pair of arms 744, a pair of opposing through holes 746, a connecting portion 748 between the pair of arms 744, and a pair of opposing elastomeric pads 750.

The pair of arms 744 includes a stationary arm 752 and a moveable arm 754. Each arm of the pair of arms 744 includes a fastener complementary to the other. For example, the stationary arm 752 can include a rack of teeth and the moveable arm 754 can include a pawl. When present, the pawl is configured to move linearly across the rack of teeth as the moveable arm 754 is moved toward the connecting portion 748 of the optical-fiber stylet holder 700.

Each through hole of the pair of through holes 746 is through at least an arm of the pair of arms 744.

An elastomeric pad of the pair of elastomeric pads 750 is disposed on the moveable 754 arm and another elastomeric pad of the pair of elastomeric pads 750 is disposed on the connecting portion 748 of the optical-fiber stylet holder 700. The pair of elastomeric pads 750 are configured to compress an optical-fiber stylet such as the optical-fiber stylet 10 inserted through the pair of through holes 746 when the moveable arm 754 is moved toward the connecting portion 748 of the optical-fiber stylet holder 700.

The optical-fiber stylet holder 700 thereby provides a locking mechanism configured to lock the optical-fiber stylet 10 in the optical-fiber stylet holder 700 and prevent distal movement of the optical-fiber stylet 10 while the optical-fiber stylet 10 is disposed in a catheter such as the catheter 16. However, the optical-fiber stylet holder 700 can be configured to couple to a Luer connector of the catheter 16 to prevent proximal movement of the optical-fiber stylet 10 as well.

Figure 8:
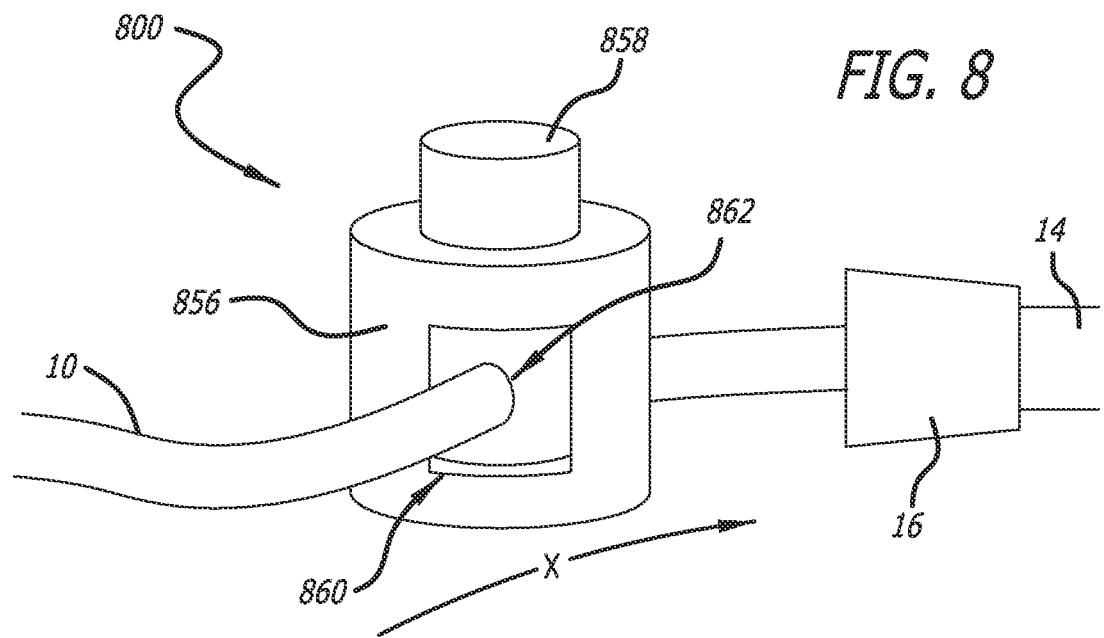
FIG. 8 illustrates an eighth optical-fiber stylet holder in accordance with some embodiments.

FIG. 8 illustrates an eighth optical-fiber stylet holder 800 in accordance with some embodiments.

As shown, the optical-fiber stylet holder 800 includes a housing 856, an insert 858, and a spring (not shown).

The housing 856 includes a housing through hole 860 dimensioned to accept an optical-fiber stylet such as the optical-fiber stylet 10 therethrough.

The insert 858 is partially disposed in the housing 856 and partially extends as a button from a side of the housing 856 perpendicular to the housing through hole 860. The insert includes an insert through hole 862 coincident with the housing through hole 860.

The spring is configured to push or pull the insert 858 toward the side of the housing 856 from which the insert 858 extends. The optical-fiber stylet 10 acts as a stop to the insert 858 being pushed or pulled toward the side of the housing 856 when the optical-fiber stylet 10 is inserted through both the housing through hole 860 and the insert through hole 862.

The optical-fiber stylet holder 800 thereby provides a locking mechanism configured to lock the optical-fiber stylet 10 in the optical-fiber stylet holder and prevent distal movement of the optical-fiber stylet 10 while the optical-fiber stylet 10 is disposed in a catheter such as the catheter 16. However, the optical-fiber stylet holder 800 can be configured to couple to a Luer connector of the catheter 16 to prevent proximal movement of the optical-fiber stylet 10 as well.

Figure 9:
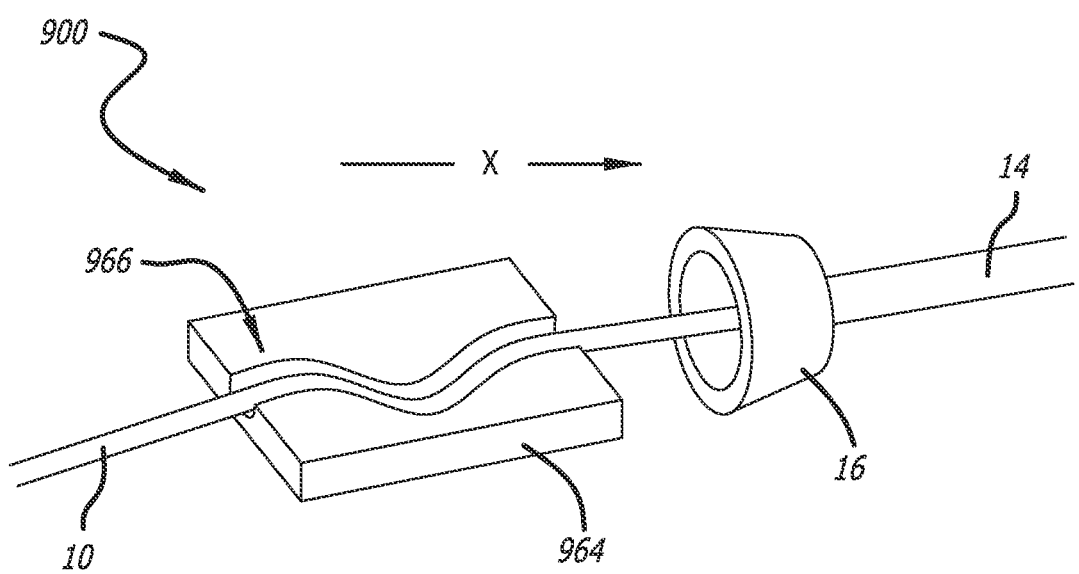
FIG. 9 illustrates a ninth optical-fiber stylet holder in accordance with some embodiments.

FIG. 9 illustrates a ninth optical-fiber stylet holder 900 in accordance with some embodiments.

As shown, the optical-fiber stylet holder 900 includes a substrate 964 and a torturous channel 966 in a side (e.g., a major side) of the substrate 964.

The torturous channel 966 is dimensioned to accept an optical-fiber stylet such as the optical-fiber stylet 10 laid therein. Advantageously, the torturous channel 966, being known, can be used for FOSS system calibration.

The optical-fiber stylet holder 900 thereby provides a locking mechanism configured to lock the optical-fiber stylet 10 in the optical-fiber stylet holder 900 and prevent distal movement of the optical-fiber stylet 10 while the optical-fiber stylet 10 is disposed in a catheter such as the catheter 16. However, the optical-fiber stylet holder 900 can be configured to couple to a Luer connector of the catheter 16 to prevent proximal movement of the optical-fiber stylet 10 as well.

FIG. 10 illustrates a tenth optical-fiber stylet 1000 holder in accordance with some embodiments.

As shown, the optical-fiber stylet holder includes a septum 1068 configured to be disposed in a Luer connector of a catheter such as the Luer connector 12 of the catheter 16.

The septum 1068 includes a through hole 1070 dimensioned to accept an optical-fiber stylet such as the optical-fiber stylet 10 therethrough and firmly hold the optical-fiber stylet 10 by friction when the optical-fiber stylet 10 is inserted therein. The septum 1068 can be formed of an elastomeric material.

The optical-fiber stylet holder 1000 can also include a retainer 1072. The retainer 1072 includes an annular rim 1074 and a plurality of wedge-shaped pieces 1076 extending from the rim 1074 and biased toward a center of the retainer 1072. The retainer 1072 is configured to slide off the Luer connector 12 and onto the optical-fiber stylet 10 bringing tips of the wedge-shaped pieces 1076 inward toward the center of the retainer 1072.

The retainer 1072 provides a secondary locking mechanism configured to prevent distal movement of the optical-fiber stylet 10 while the optical-fiber stylet 10 is disposed in a catheter such as the catheter 16. Indeed, on account of the wedge-shaped pieces 1076 of the retainer 1072 being lodged against the optical-fiber stylet 10, the optical-fiber stylet 10 is prevented from distal movement.

The optical-fiber stylet holder thereby provides a primary locking mechanism in the septum 1070 that is configured to lock the optical-fiber stylet 10 in the optical-fiber stylet holder 1000 and prevent both proximal and distal movement of the optical-fiber stylet 10 while the optical-fiber stylet 10 is disposed in the catheter 16. The optical-fiber stylet holder also thereby provides a secondary locking mechanism configured in the retainer 1072 that is configured to lock the optical-fiber stylet 10 in the optical-fiber stylet holder 900 and prevent distal movement of the optical-fiber stylet 10 while the optical-fiber stylet 10 is disposed in the catheter 16.

Methods

Methods include methods of using the optical-fiber stylet holders 100-1000 disclosed herein. For example, a method of an optical-fiber stylet holder 100, 200, 300, 400, 500, 600, 700, 800, 900, or 1000 includes a stylet-inserting step, a first stylet-advancing step, a second stylet-advancing step, and a stylet-holding step.

The stylet-inserting step includes inserting an optical-fiber stylet such as the optical-fiber stylet 10 into the optical-fiber stylet holder 100, 200, 300, 400, 500, 600, 700, 800, 900, or 1000. The first stylet-advancing step includes advancing the optical-fiber stylet 10 through a catheter such as the catheter 16. The second stylet-advancing step includes advancing a distal tip of the optical-fiber stylet 10 through a vasculature to a target anatomical location in a patient. The stylet-holding step includes holding the distal tip of the optical-fiber stylet 10 in the target anatomical location without at least distal advancement of the distal tip by locking the optical-fiber stylet in the optical-fiber stylet holder 100, 200, 300, 400, 500, 600, 700, 800, 900, or 1000.

Again, FIG. 1 illustrates the first optical-fiber stylet holder 100 in accordance with some embodiments.

The method can further include a stylet-placing step, a first stylet-pressing step, and a second stylet-pressing step.

The stylet-placing step includes placing the optical-fiber stylet 10 against the radiused shoulder 104 of the integrated funnel 102 of the optical-fiber stylet holder 100.

The first stylet-pressing step includes pressing the optical-fiber stylet 10 against a side-wall petal of the plurality of side-wall petals 110 about the mouth of the integrated funnel 102 to direct the optical-fiber stylet 10 into an adjacent notch of the plurality of notches 108 about the mouth of the integrated funnel 102.

The second stylet-pressing step includes pressing the optical-fiber stylet 10 into a notch of the plurality of notches 108, thereby locking the optical-fiber stylet 10 in the optical-fiber stylet holder 100 and holding the distal tip of the optical-fiber stylet 10 in the target anatomical location.

Again, FIG. 2 illustrates the second optical-fiber stylet holder 200 in accordance with some embodiments.

The method can further include the stylet-placing step and a mouth-covering step.

Again, the stylet-placing step includes placing the optical-fiber stylet 10 against the radiused shoulder 104 of the integrated funnel 102 of the optical-fiber stylet holder 200.

The mouth-covering step includes covering the mouth of the integrated funnel 102 with the cap 212 coupled to the side wall of the optical-fiber stylet holder 200 by the living hinge 214, thereby locking the optical-fiber stylet 10 in the optical-fiber stylet holder 200 and holding the distal tip of the optical-fiber stylet 10 in the target anatomical location.

Again, FIG. 3 illustrates the third optical-fiber stylet holder 300 in accordance with some embodiments.

The method can further include a cap-screwing step and a compressing step.

The cap-screwing step includes screwing the cap 316 of the optical-fiber stylet holder 300 onto the insertable piece.

The compressing step includes compressing around the optical-fiber stylet 10 the cylindrical gasket 318 disposed in the cap 316 between a proximal end of the cap 316 and the insertable piece with the screwing of the cap 316 onto the insertable piece, thereby locking the optical-fiber stylet 10 in the optical-fiber stylet holder 300 and holding the distal tip of the optical-fiber stylet 10 in the target anatomical location.

Again, FIG. 4 illustrates the fourth optical-fiber stylet holder 400 in accordance with some embodiments.

The stylet-inserting step can further include following the torturous path with the optical fiber stylet 10 through the plurality of rollers 424 mounted on the pair of arms 422 biased toward the centerline of the optical-fiber stylet holder 400, thereby locking the optical-fiber stylet 10 in the optical-fiber stylet holder 400 and holding the distal tip of the optical-fiber stylet 10 in the target anatomical location.

Again, FIG. 5 illustrates the fifth optical-fiber stylet holder 500 in accordance with some embodiments.

The method can further include a clamp-opening step and a clamp-closing step.

The clamp-opening step includes opening the clamp 526 of the optical-fiber stylet holder 500 before the stylet-inserting step.

The clamp-closing step includes closing the second jaw 530 of the clamp 526 onto the first jaw 528 of the clamp 526 with the optical-fiber stylet 10 between the second jaw 530 and the first jaw 528, thereby locking the optical-fiber stylet 10 in the optical-fiber stylet holder 500 and holding the distal tip of the optical-fiber stylet 10 in the target anatomical location.

Again, FIG. 6A illustrates the sixth optical-fiber stylet holder 600 in accordance with some embodiments.

The method can further include a hinge-closing step.

The hinge-closing step includes closing the pair of hinge plates 636 of the optical-fiber stylet holder 600 to compress the optical-fiber stylet 10 with the elastomeric pad 640 of a hinge plate of the pair of hinge plates 636 against another hinge plate of the pair of hinge plates 636, thereby locking the optical-fiber stylet 10 in the optical-fiber stylet holder 600 and holding the distal tip of the optical-fiber stylet 10 in the target anatomical location.

Again, FIG. 7A illustrates the seventh optical-fiber stylet holder 700 in accordance with some embodiments.

The stylet-inserting step can further include inserting the optical-fiber stylet 10 into the pair of opposing through holes 746 through the pair of arms 744 including the stationary arm 752 and the moveable arm 754.

The method can further include a pawl-moving step.

The pawl-moving step includes moving the pawl of the moveable arm 754 against the rack of teeth of the stationary arm 752 to compress the optical-fiber stylet 10 between the elastomeric pad disposed on the moveable arm 754 and the other elastomeric pad disposed on the connecting portion 748 of the optical-fiber stylet holder 700 between the pair of arms 744, thereby locking the optical-fiber stylet 10 in the optical-fiber stylet holder 700 and holding the distal tip of the optical-fiber stylet 10 in the target anatomical location.

Again, FIG. 8 illustrates the eighth optical-fiber stylet holder 800 in accordance with some embodiments.

The method can further include a button-pressing step and a button-releasing step.

The button-pressing step includes pressing the button of the insert 858 extending from the side of the housing 856 of the optical-fiber stylet holder 800 to pull or push the spring to allow the optical-fiber stylet 10 to freely move through both housing and insert through holes 860 and 862 for adjusting a position of the optical-fiber stylet holder 800 on the optical-fiber stylet 10.

The button-releasing step includes releasing the button to push or pull the insert 858 by way of the spring toward the side of the housing 856 from which the insert 858 extends, thereby locking the optical-fiber stylet 10 in the optical-fiber stylet holder 800 as a stop in the housing and insert through holes 860 and 862 and holding the distal tip of the optical-fiber stylet 10 in the target anatomical location.

Again, FIG. 9 illustrates the ninth optical-fiber stylet holder 900 in accordance with some embodiments.

The stylet-inserting step can further include laying the optical-fiber stylet 10 into the torturous channel 966 in the side of the substrate 964 of the optical-fiber stylet holder 900, thereby locking the optical-fiber stylet 10 in the optical-fiber stylet holder 900 and holding the distal tip of the optical-fiber stylet 10 in the target anatomical location.

Again, FIG. 10 illustrates the tenth optical-fiber stylet holder 1000 in accordance with some embodiments.

The stylet-inserting step can further include inserting the optical-fiber stylet 10 into the through hole 1070 of the septum 1068 of the optical-fiber stylet holder 1000, thereby locking the optical-fiber stylet 10 in the optical-fiber stylet holder 1000 by friction and holding the distal tip of the optical-fiber stylet 10 in the target anatomical location.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An optical-fiber stylet holder, comprising:
   an integrated funnel including:
      a radiused shoulder having a radius configured to allow an optical-fiber stylet to be placed against the radiused shoulder without breakage of one or more optical fibers in the optical-fiber stylet; and
      a neck configured to be coincident with a lumen of an extension leg of a catheter, the neck having an inner diameter sufficient to accept the optical-fiber stylet.

2. The optical-fiber stylet holder of claim 1, further comprising:
   a locking mechanism configured to lock the optical-fiber stylet in the optical-fiber stylet holder.

3. The optical-fiber stylet holder of claim 2, wherein the locking mechanism includes a plurality of notches about a mouth of the integrated funnel through a side wall of the optical-fiber stylet holder, each notch of the plurality of notches sized to firmly hold the optical-fiber stylet when the optical-fiber stylet is pressed therein.

4. The optical-fiber stylet holder of claim 3, wherein the locking mechanism includes a plurality of side-wall petals about the mouth of the integrated funnel alternating with the plurality of notches, each side-wall petal of the plurality of side-wall petals configured to direct the optical-fiber stylet into an adjacent notch when the optical-fiber stylet is pressed thereagainst.

5. The optical-fiber stylet holder of claim 2, wherein the locking mechanism includes a cap configured to cover a mouth of the integrated funnel and the optical-fiber stylet when extending from the mouth, the cap coupled to a side wall of the optical-fiber stylet holder by a living hinge.

6. The optical-fiber stylet holder of claim 1, wherein the optical-fiber stylet holder is integral with a Luer connector of the catheter.

7. The optical-fiber stylet holder of claim 1, wherein the optical-fiber stylet holder is a cap including internal threads in a distal portion of the cap configured to screw onto external threads of a Luer connector of the catheter.

8. An optical-fiber stylet holder, comprising:
   a cap including:
      internal threads in a distal portion of a bore of the cap configured to screw onto complementary external threads of an insertable piece; and
      a cap through hole in a proximal end of the cap having an inner diameter sufficient to accept an optical-fiber stylet;
   a cylindrical gasket of a compressible material, the gasket including a gasket through hole having an inner diameter no smaller than that of the cap through hole; and
   a locking mechanism defined by the gasket disposed in the cap between the proximal end of the cap and the insertable piece, the locking mechanism configured to lock the optical-fiber stylet in the optical-fiber stylet holder by compression of the gasket when the cap is screwed onto the insertable piece with the optical-fiber stylet in the optical-fiber stylet holder.

9. The optical-fiber stylet holder of claim 8, wherein the compression of the gasket is axial compression between the proximal end of the cap and the insertable piece, the axial compression, in turn, providing radial compression around the optical-fiber stylet to lock the optical-fiber stylet in the optical-fiber stylet holder.

10. The optical-fiber stylet holder of claim 8, wherein the insertable piece is part of a male Luer connector of a catheter.

11. The optical-fiber stylet holder of claim 8, wherein the insertable piece is part of the optical-fiber stylet holder, the insertable piece having a distal portion configured as a female Luer connector.

12. An optical-fiber stylet holder, comprising:
   a pair of arms biased toward a centerline of the optical-fiber stylet holder;
   a plurality of rollers mounted on the pair of arms, consecutive rollers of the plurality of rollers alternating from arm to arm of the pair of arms forming a tortuous path for an optical-fiber stylet to follow between the pair of arms; and
   a locking mechanism defined by the tortuous path, the locking mechanism configured to lock the optical-fiber stylet in the optical-fiber stylet holder by friction through a combination of the pair of arms being biased toward the centerline of the optical-fiber stylet holder and the tortuous path formed between the pair or arms.

13. The optical-fiber stylet holder of claim 12, wherein the optical-fiber stylet holder is integral with a Luer connector of a catheter.

14. The optical-fiber stylet holder of claim 12, wherein the optical-fiber stylet holder is a cap including internal threads in a distal portion of the cap configured to screw onto external threads of a Luer connector of a catheter.

15. An optical-fiber stylet holder, comprising:
a clamp including:
a first jaw;
a second jaw, the first jaw and the second jaw longitudinally extending in a same direction as that of a centerline of the optical-fiber stylet holder; and
an elastic piece configured to store mechanical energy coupled to both the first jaw and the second jaw, the elastic piece configured to hold the second jaw against the first jaw;
a through hole through a distal end of the optical-fiber stylet holder coincident with a lumen of an extension leg of a catheter; and
a locking mechanism defined by the clamp, the locking mechanism configured to lock an optical-fiber stylet in the optical-fiber stylet holder by friction of the clamp along a length of the optical-fiber stylet.

16. The optical-fiber stylet holder of claim 15, wherein the optical-fiber stylet holder is integral with a Luer connector of the catheter.

17. The optical-fiber stylet holder of claim 15, wherein the optical-fiber stylet holder is a cap including internal threads in a distal portion of the cap configured to screw onto external threads of a Luer connector of the catheter.

18. An optical-fiber stylet holder, comprising:
a pair of hinge plates, each hinge plate of the pair of hinge plates including a fastener complementary to the other hinge plate;
a hinge formed between the pair of hinge plates, an optical-fiber stylet providing a hinge pin of the hinge; and
an elastomeric pad disposed on a hinge plate of the pair of hinge plates configured to compress the optical-fiber stylet against another hinge plate of the pair of hinge plates when the pair of hinge plates are closed, the optical-fiber stylet holder thereby providing a locking mechanism configured to lock the optical-fiber stylet in the optical-fiber stylet holder and prevent distal movement of the optical-fiber stylet while the optical-fiber stylet is disposed in a catheter.

19. The optical-fiber stylet holder of claim 18, wherein the optical-fiber stylet holder is configured to couple to a Luer connector of the catheter.

* * * * *